United States Patent
Forlivio et al.

(10) Patent No.: US 10,412,967 B2
(45) Date of Patent: Sep. 17, 2019

(54) PLANT AND CROP GROWTH REGULATING/BIOSTIMULANT FORMULATIONS AND METHODS OF USE

(71) Applicant: Arysta Lifescience North America, LLC, Cary, NC (US)

(72) Inventors: Daniel Marques Forlivio, Sao Paulo-SP (BR); Pablo Alberto Kalnay, Sao Paulo-SP (BR); Giuvan Lenz, Pereiras-SP (BR); Roberto De Oliveira Rodrigues, Pereiras (BR); Joao Massayuki Miyasaki, Sao Paulo-SP (BR)

(73) Assignee: ARYSTA LIFESCIENCE NORTH AMERICA, LLC, Cary, NC (US)

( * ) Notice: Subject to any disclaimer, the term of this patent is extended or adjusted under 35 U.S.C. 154(b) by 0 days.

(21) Appl. No.: 15/526,028

(22) PCT Filed: Nov. 19, 2015

(86) PCT No.: PCT/US2015/061681
§ 371 (c)(1),
(2) Date: May 11, 2017

(87) PCT Pub. No.: WO2016/081768
PCT Pub. Date: May 26, 2016

(65) Prior Publication Data
US 2017/0318812 A1 Nov. 9, 2017

Related U.S. Application Data

(60) Provisional application No. 62/083,020, filed on Nov. 21, 2014, provisional application No. 62/086,282, filed on Dec. 2, 2014.

(51) Int. Cl.
*A01N 47/38* (2006.01)
*A01N 25/30* (2006.01)

(52) U.S. Cl.
CPC ............. *A01N 47/38* (2013.01); *A01N 25/30* (2013.01); *A01N 2300/00* (2013.01)

(58) Field of Classification Search
None
See application file for complete search history.

(56) References Cited

U.S. PATENT DOCUMENTS

| | | |
|---|---|---|
| 3,737,298 A | 6/1973 | Fielding |
| 6,077,814 A | 6/2000 | Morita et al. |
| 2013/0137573 A1* | 5/2013 | Chung .................. A01N 43/16 504/103 |

FOREIGN PATENT DOCUMENTS

| | | | |
|---|---|---|---|
| WO | 2010046417 | | 4/2010 |
| WO | WO2011073616 | * | 6/2011 |

* cited by examiner

*Primary Examiner* — Alton N Pryor
(74) *Attorney, Agent, or Firm* — Cantor Colburn LLP

(57) ABSTRACT

A method of stimulating or promoting plant growth includes applying to a crop plant a composition of ipfencarbazone in an amount sufficient to stimulate or promote plant growth. In some aspects, embodiments herein provide methods of stimulating or promoting plant growth comprising applying to a crop plant a composition comprising ipfencarbazone in an amount sufficient to stimulate or promote plant growth.

32 Claims, 31 Drawing Sheets

PLANT AND CROP GROWTH REGULATING/BIOSTIMULANT FORMULATIONS AND METHODS OF USE

CROSS REFERENCE TO RELATED APPLICATIONS

This application claims the priority benefit of U.S. Provisional Application No. 62/083,020 filed on Nov. 21, 2014 and entitled "PLANT AND CROP GROWTH REGULATING/BIOSTIMULANT FORMULATIONS AND METHODS OF USE" and U.S. Provisional Application No. 62/086,282, filed Dec. 2, 2014 and entitled "PLANT AND CROP GROWTH REGULATING/BIOSTIMULANT FORMULATIONS AND METHODS OF USE" which are incorporated herein by reference.

INTRODUCTION

The invention relates to methods and compositions for stimulating plant growth. In particular, the invention relates to the use of ipfencarbazone, known as a pre-emergent herbicide, for stimulating or promoting plant growth.

Plant growth stimulators are used in many crops to increase biomass, manage the rate of growth and to increase yield and quality. These products are also used to manage abiotic stresses such as cold stress, drought stress, and the like.

SUMMARY

In some aspects, embodiments herein provide methods of stimulating or promoting plant growth comprising applying to a crop plant a composition comprising ipfencarbazone in an amount sufficient to stimulate or promote plant growth.

BRIEF DESCRIPTION OF DRAWINGS

Various embodiments of the invention will be described herein below with reference to the figures wherein.

Figure 11:
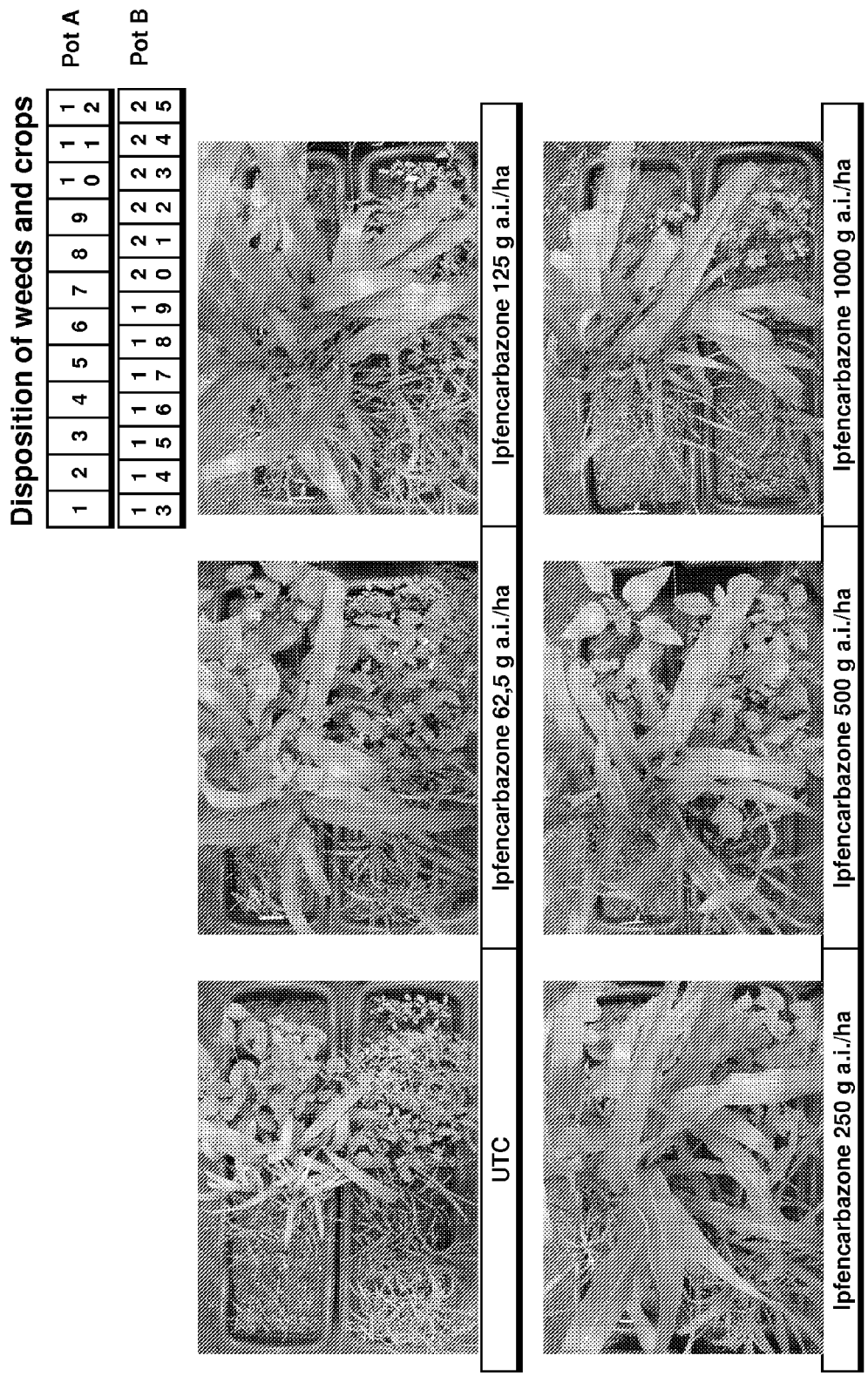
Figure 12:
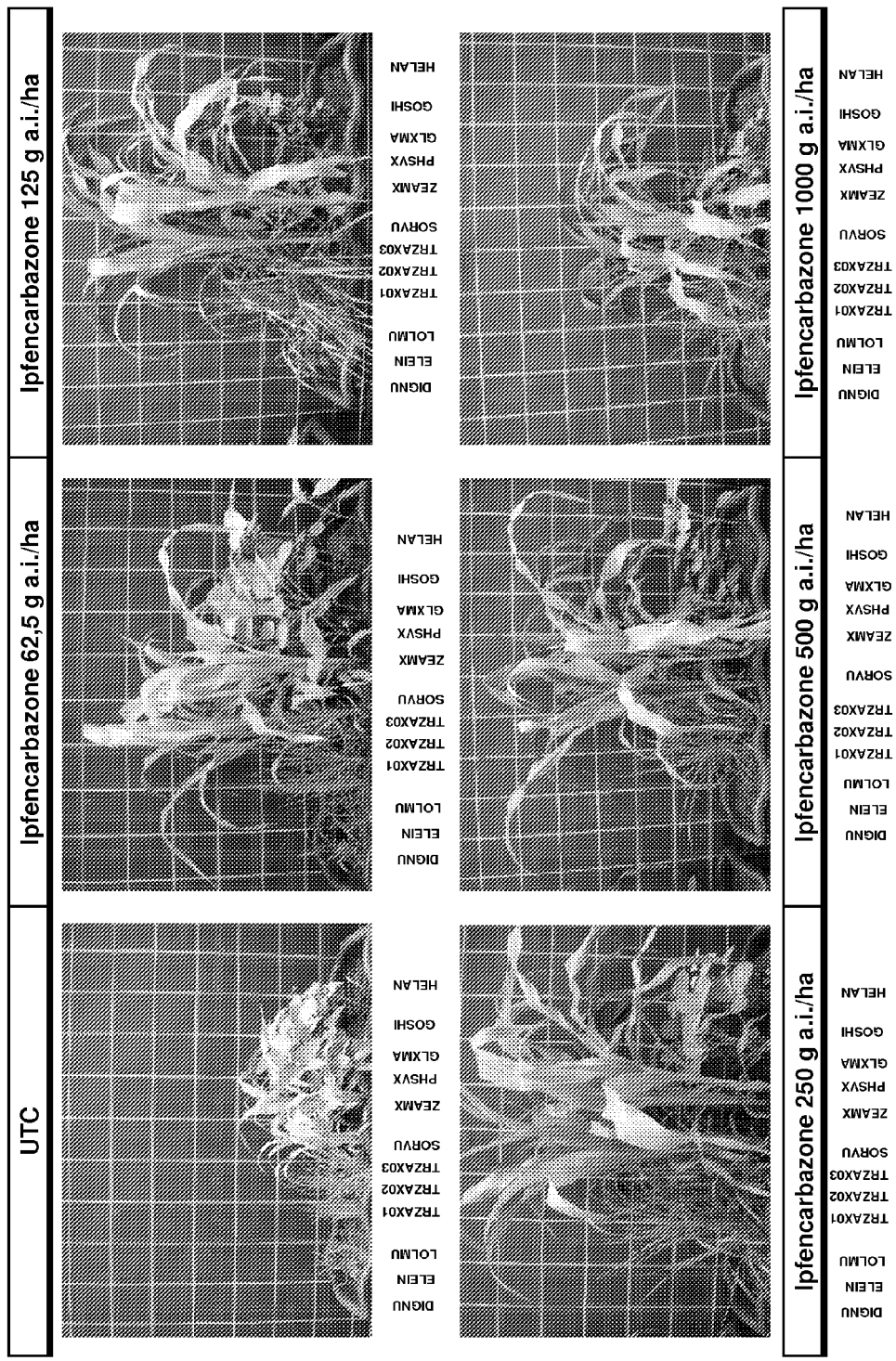
Figure 13:
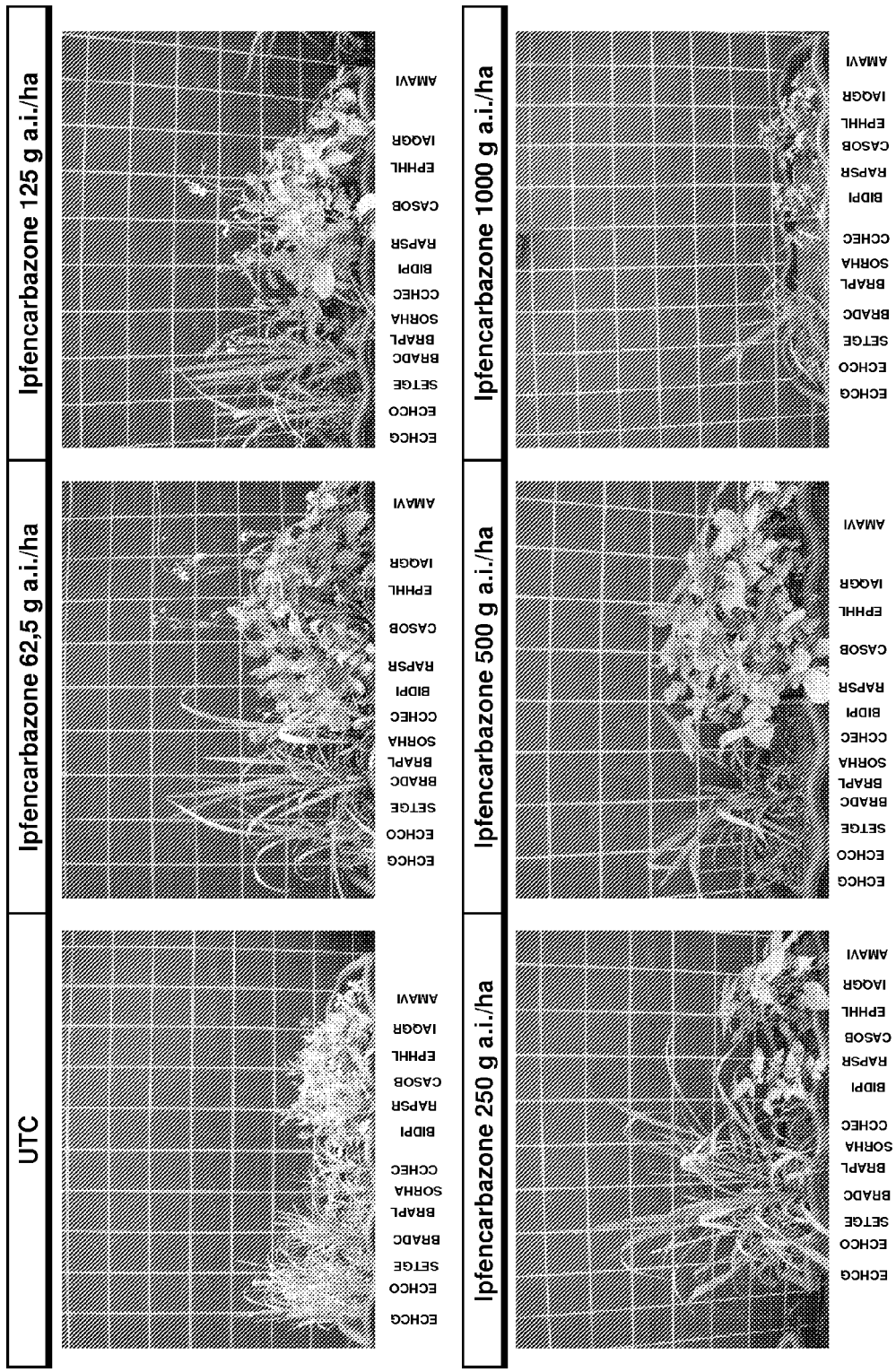
Figure 14:
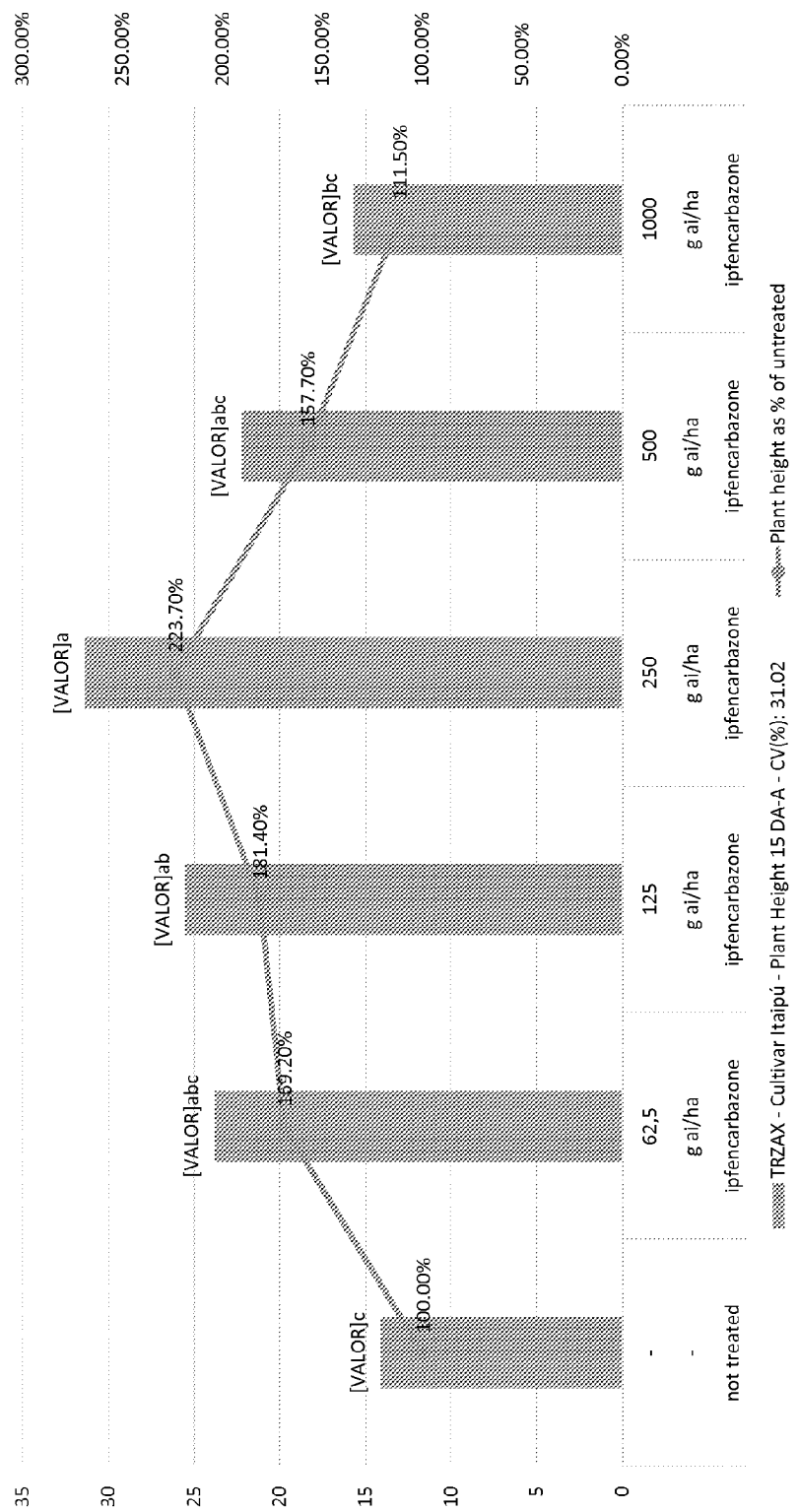
Figure 15:
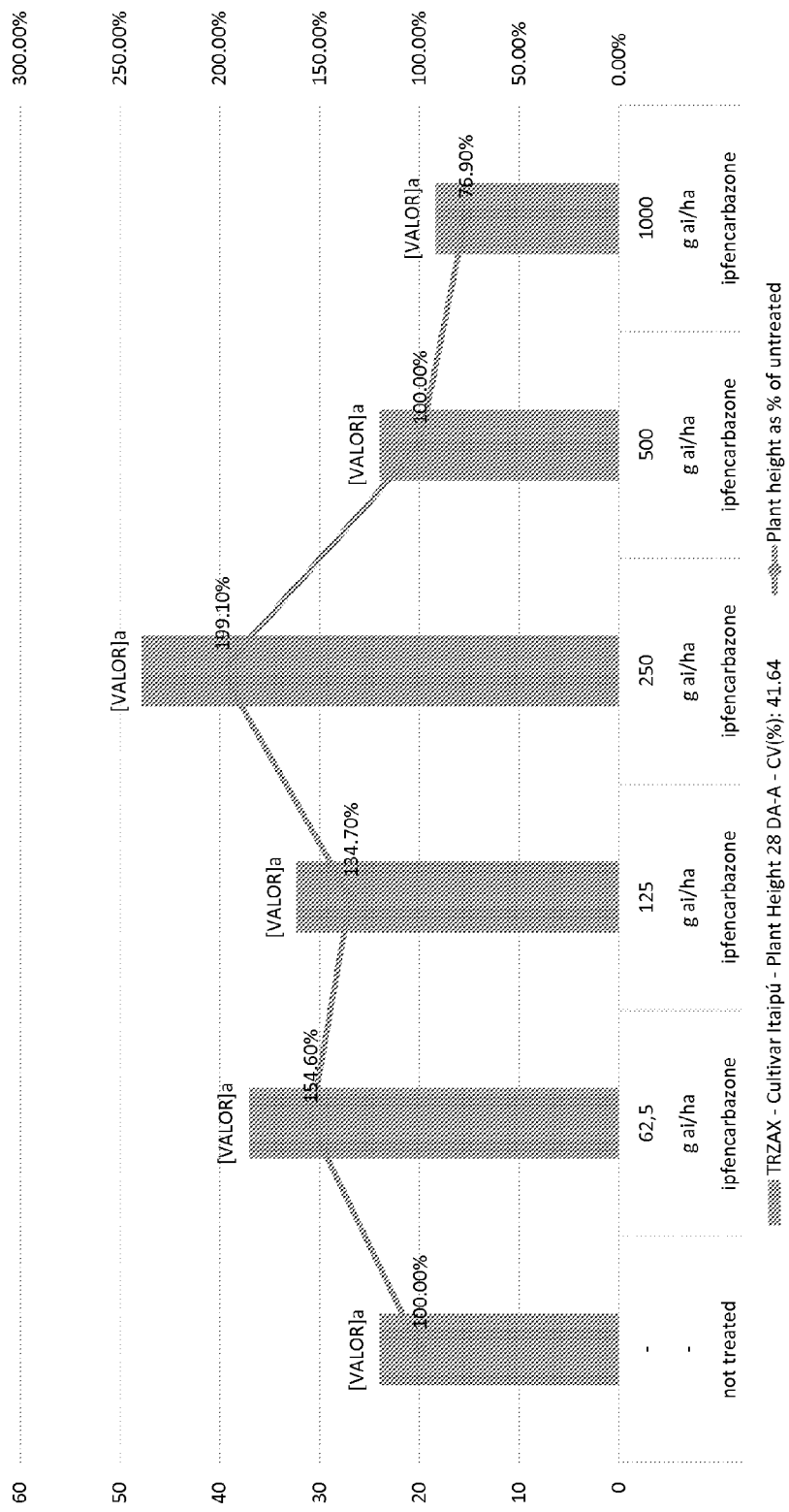
Figure 16:
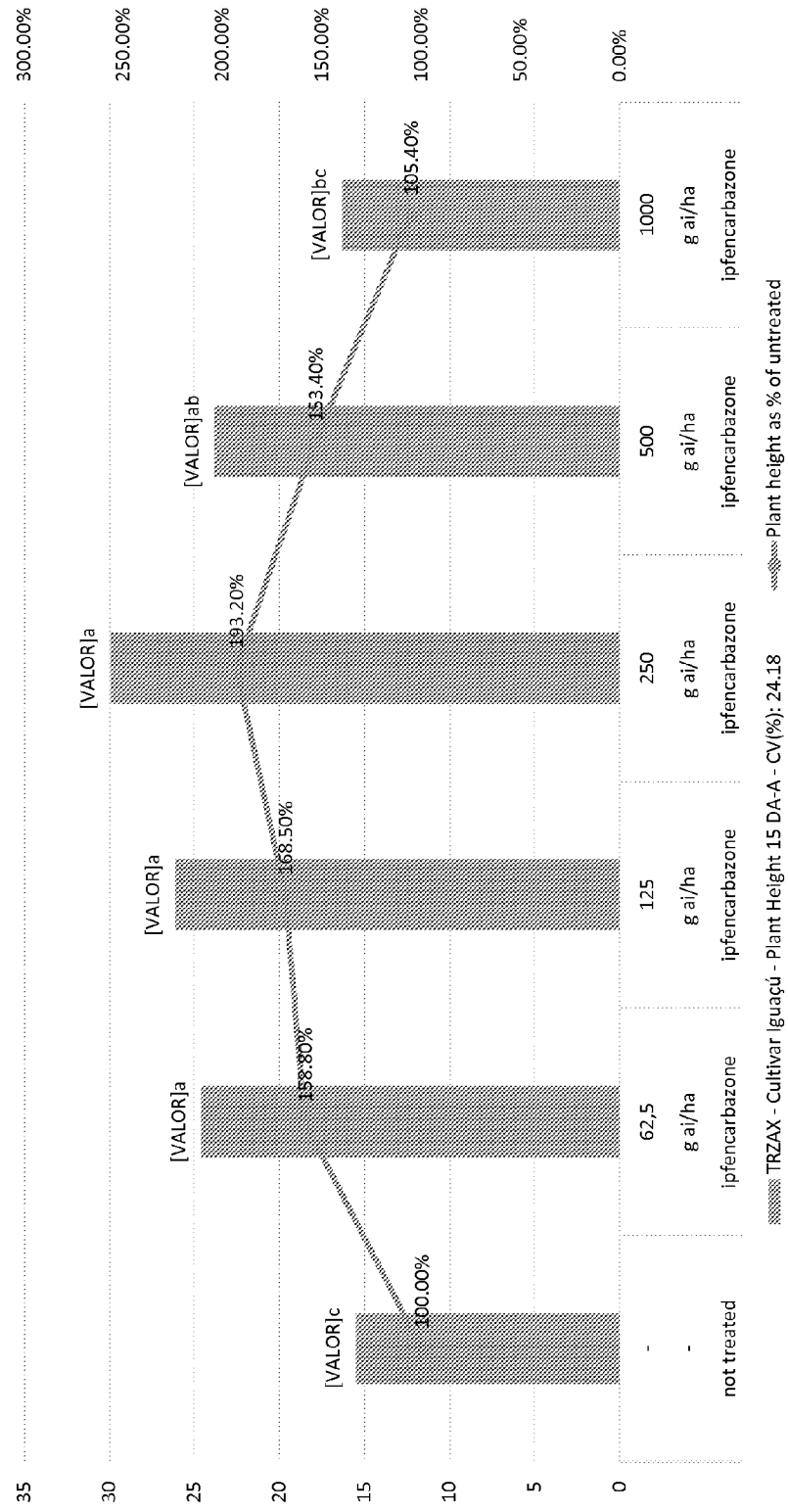
Figure 17:
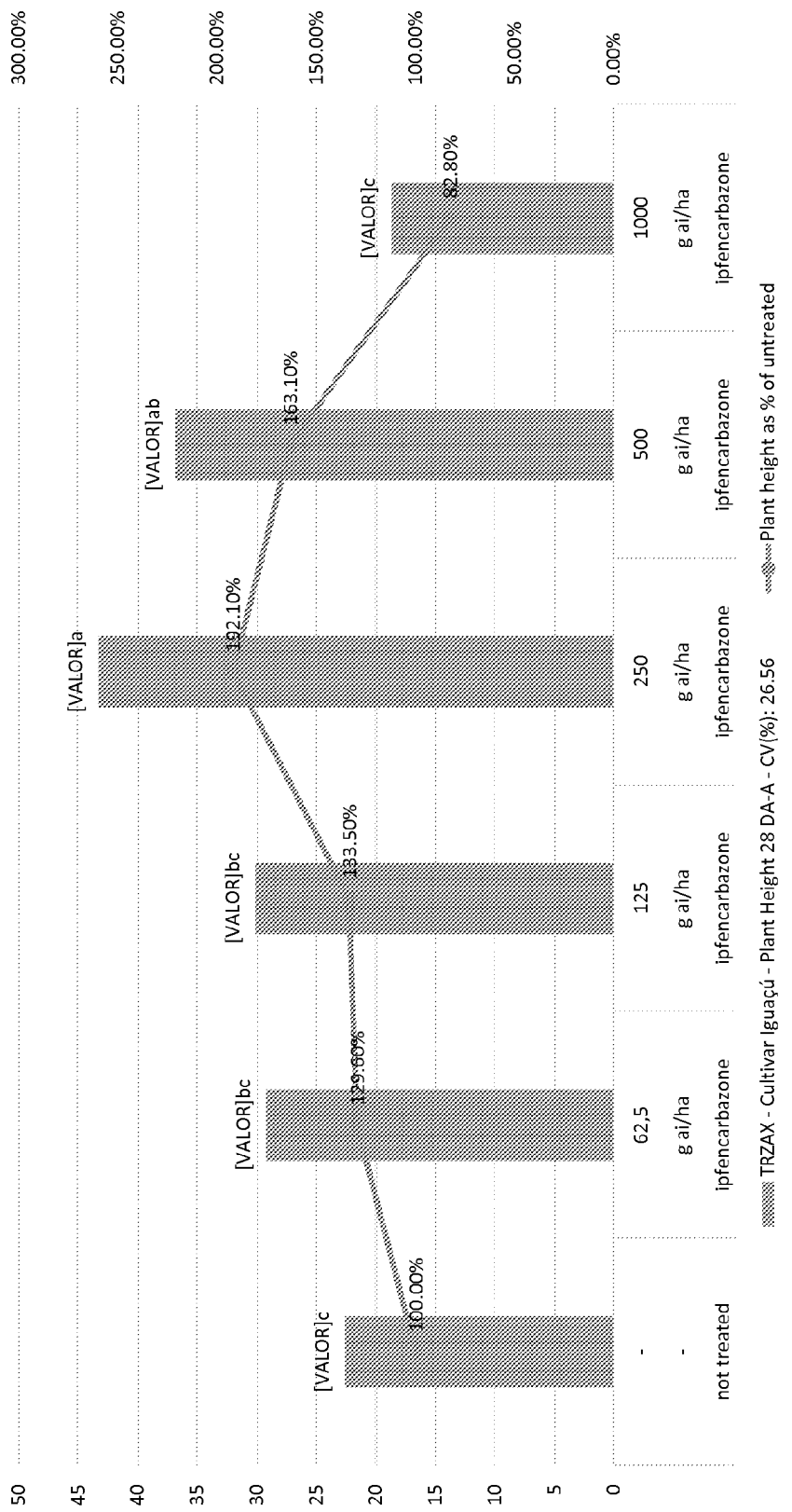
Figure 18:
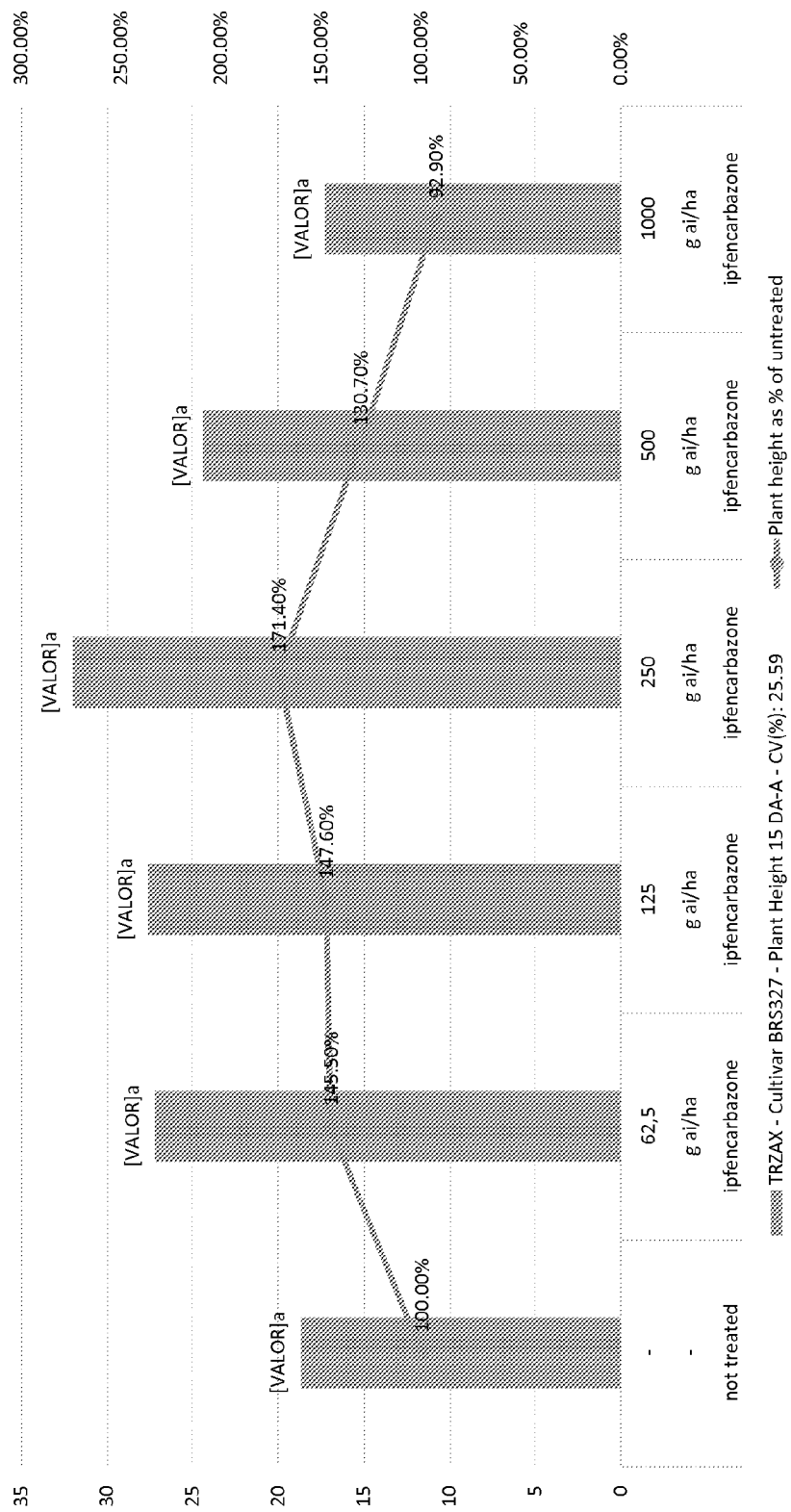
Figure 19:
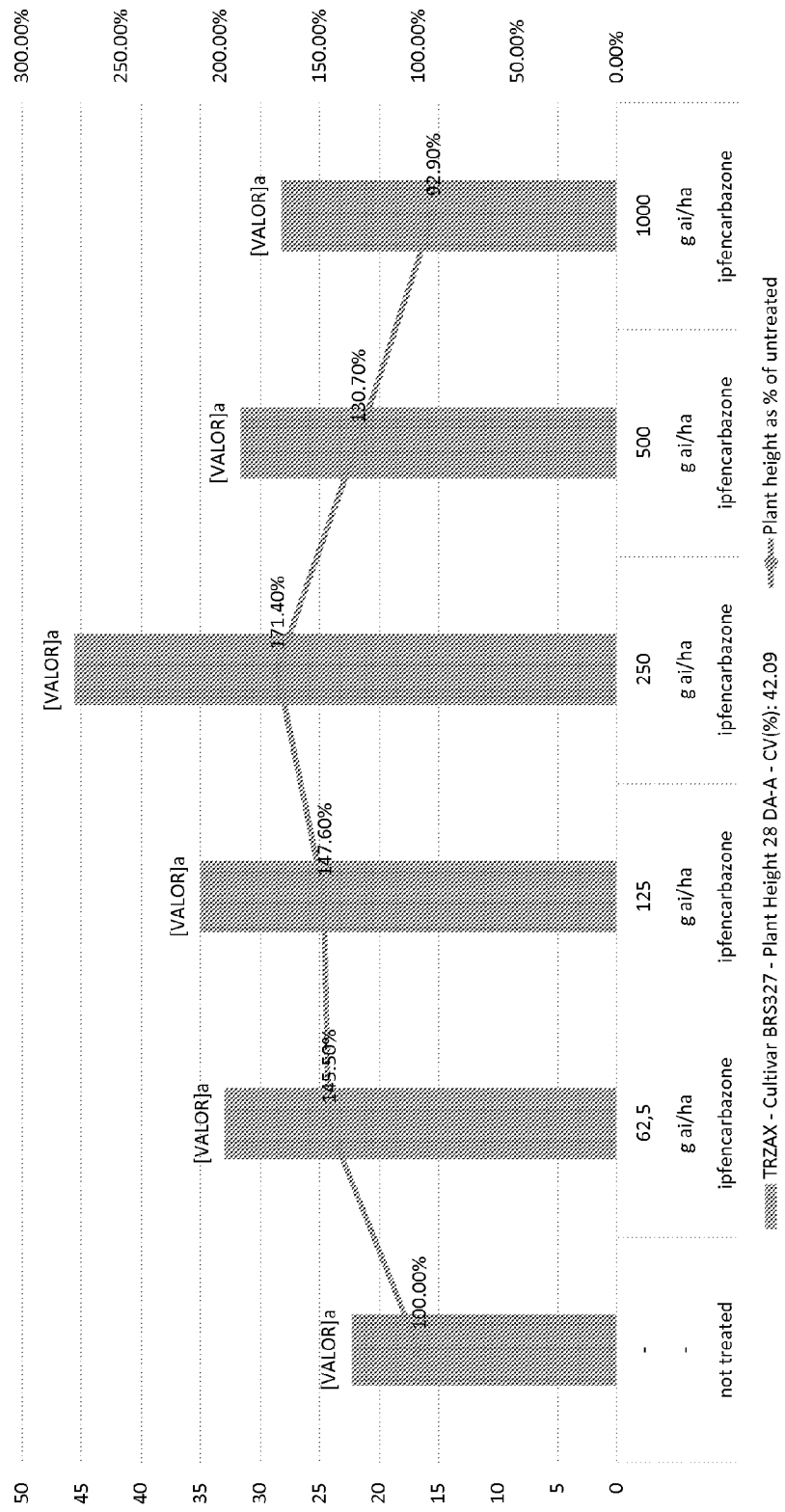
Figure 20:
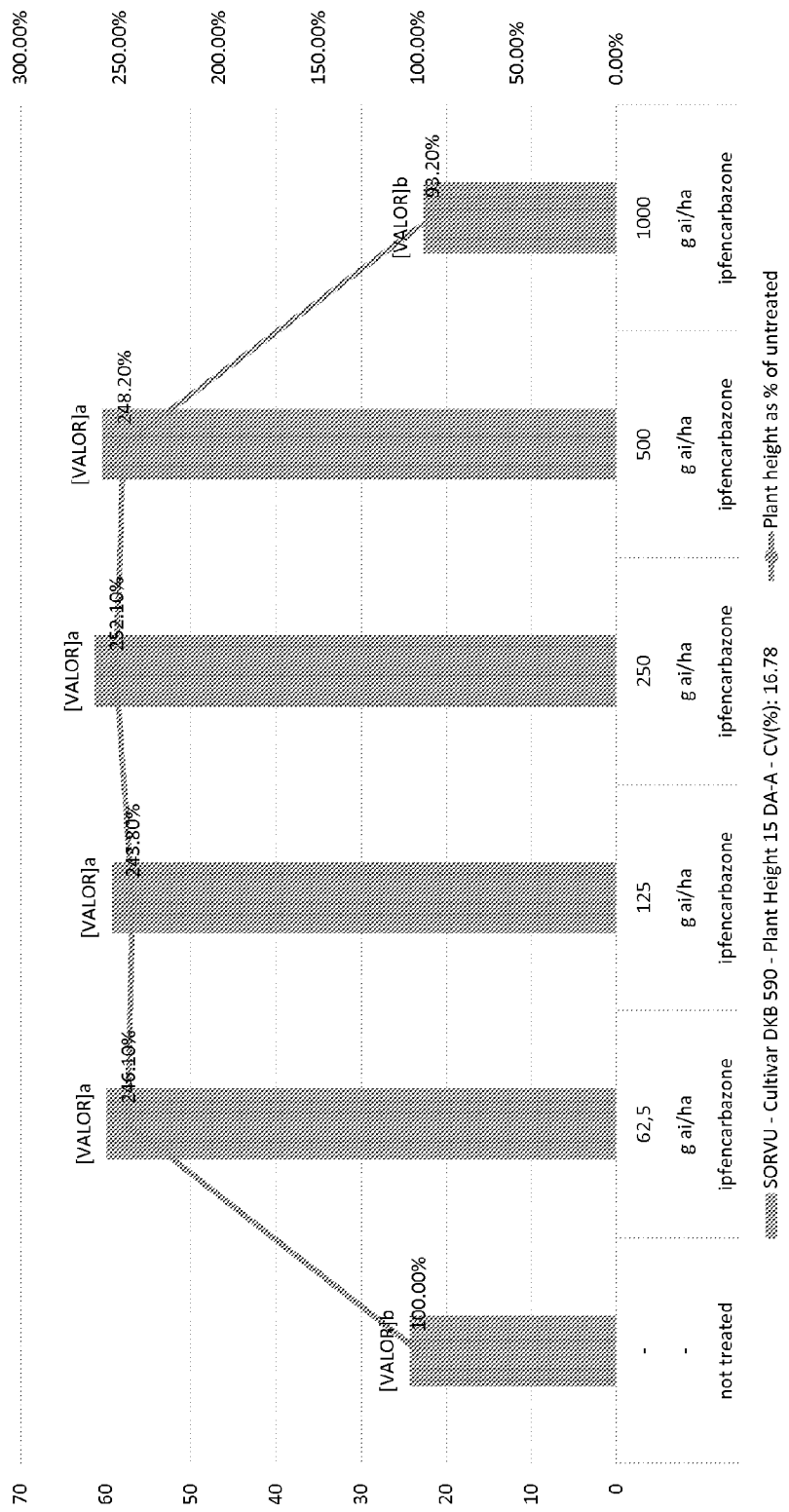
Figure 21:
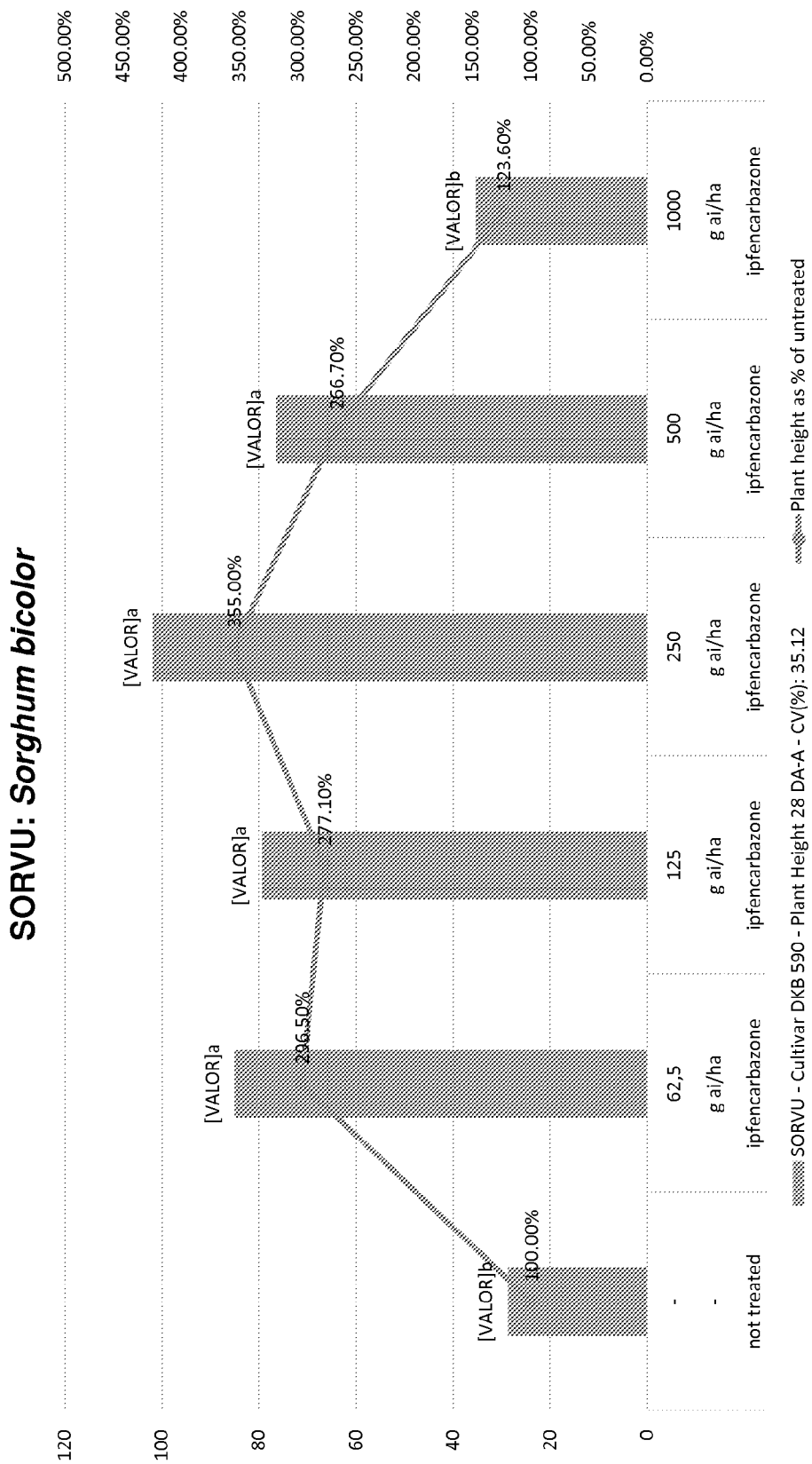
Figure 22:
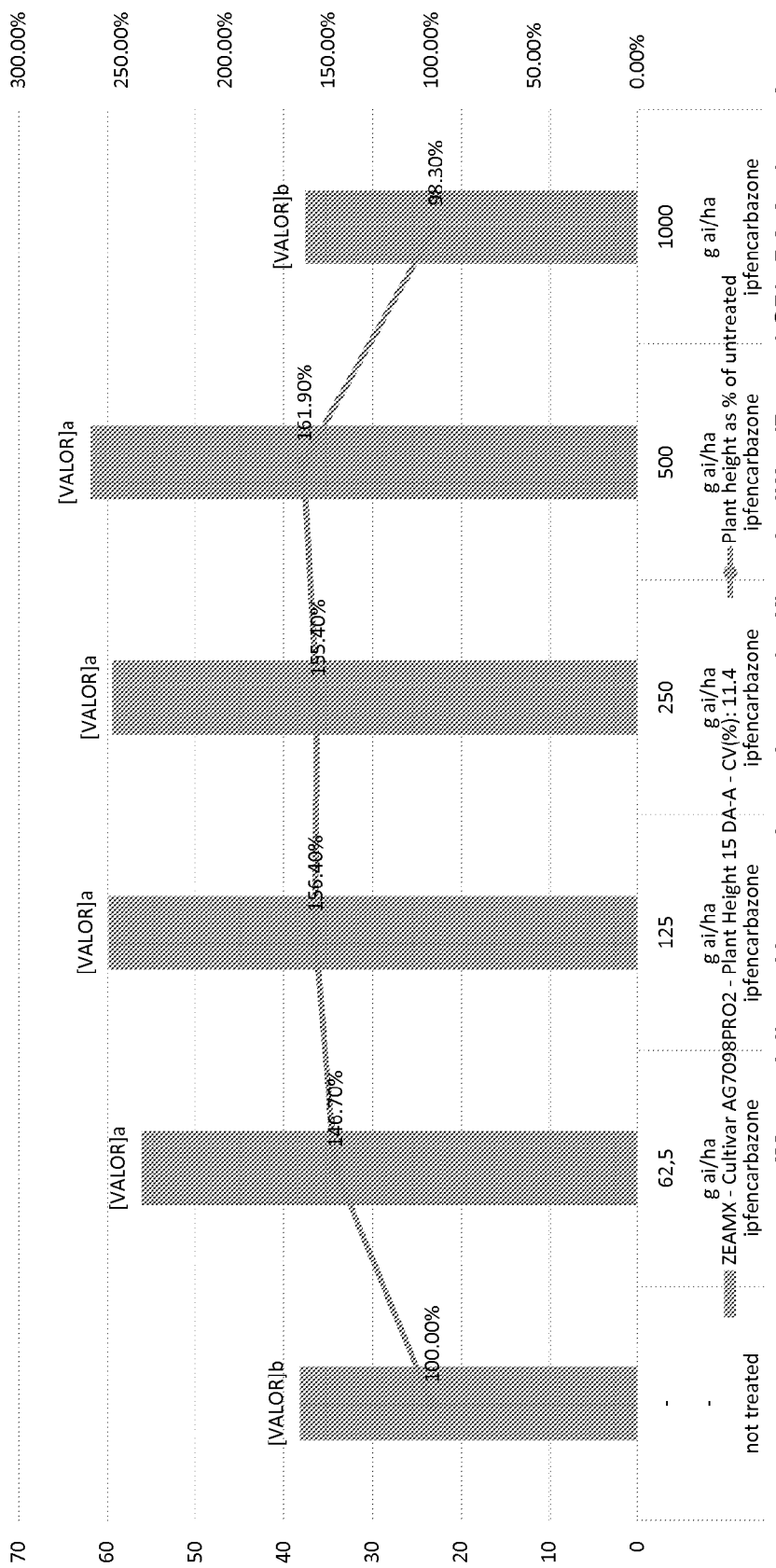
Figure 23:
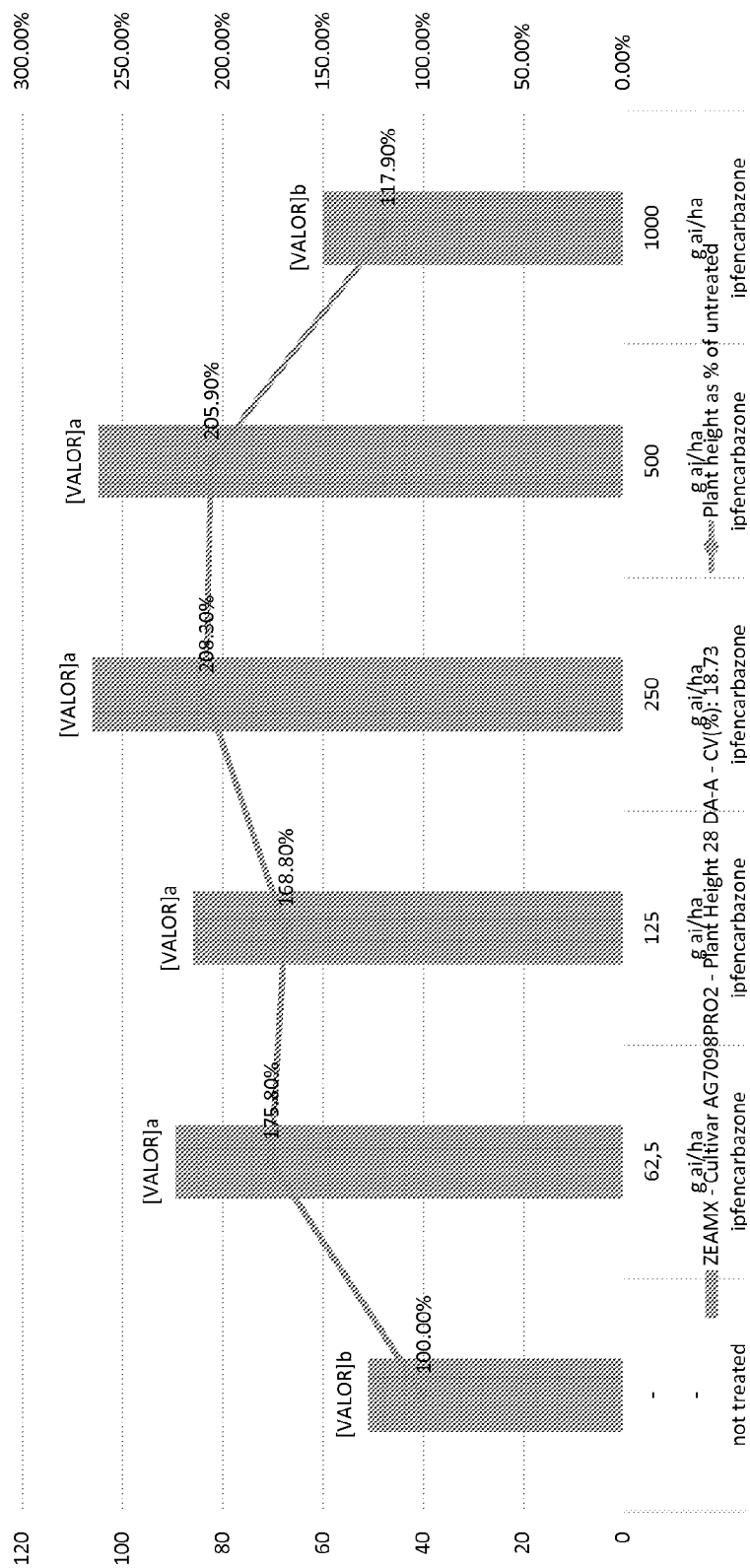
Figure 24:
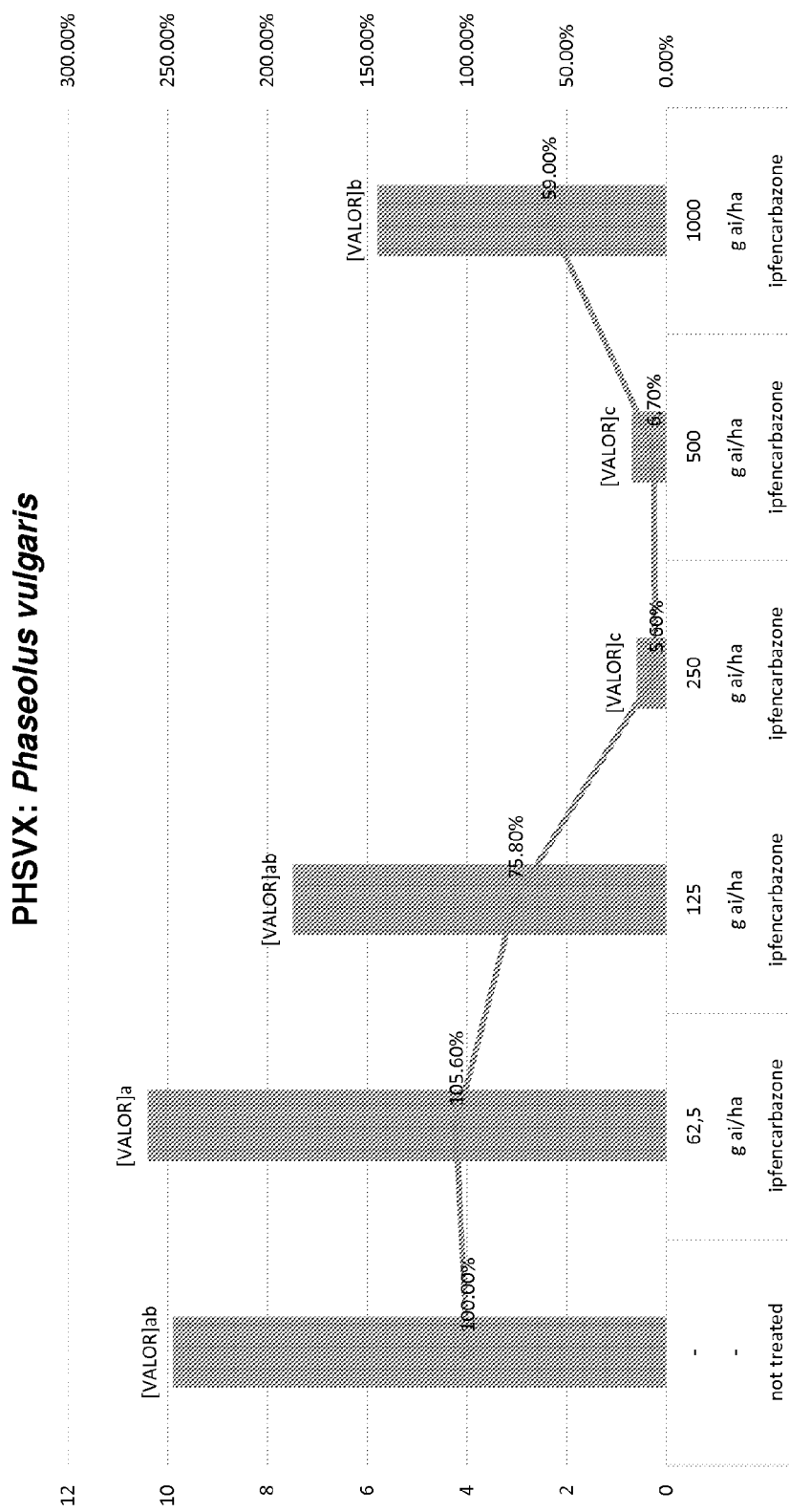
Figure 25:
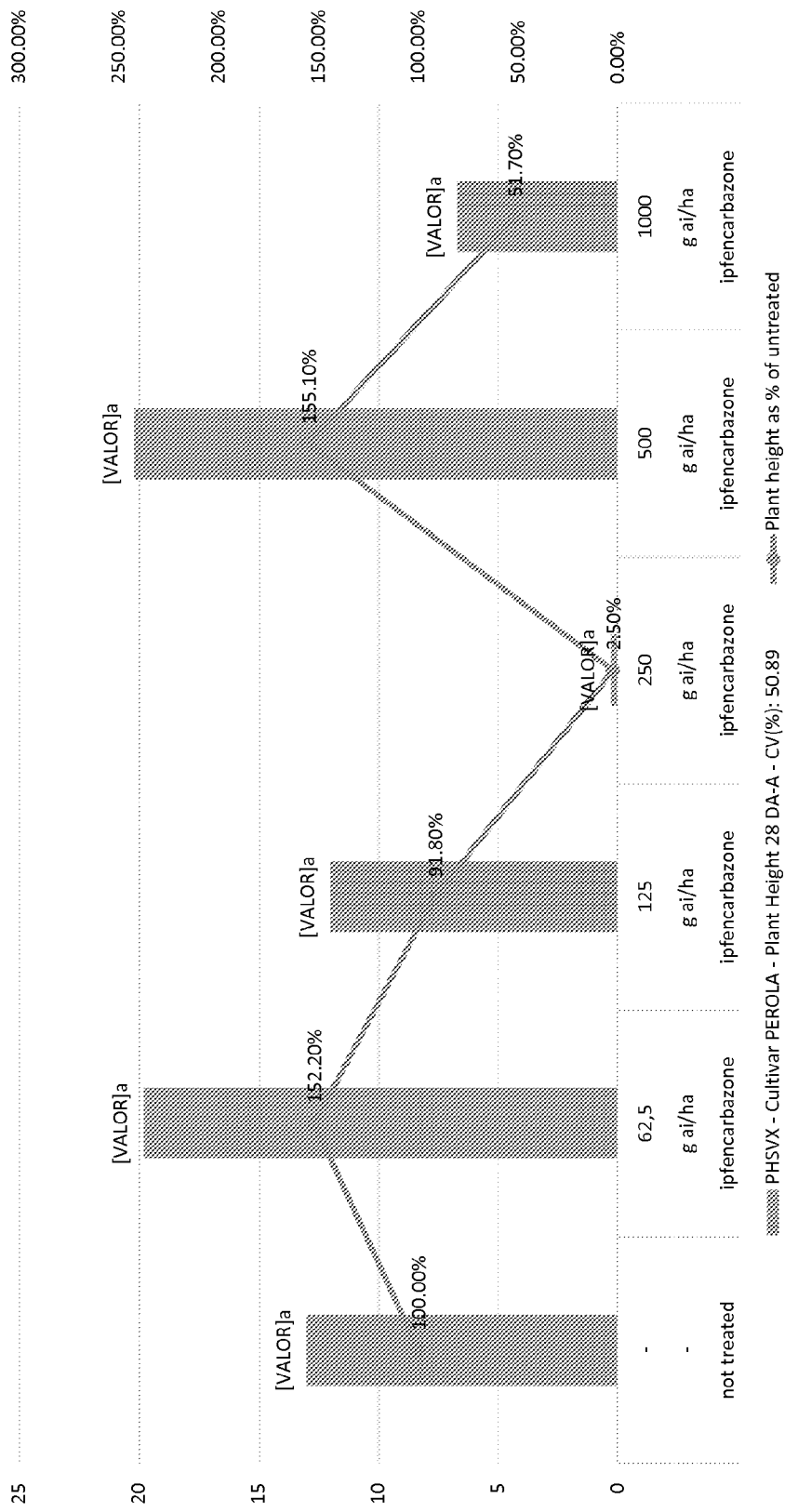
Figure 26:
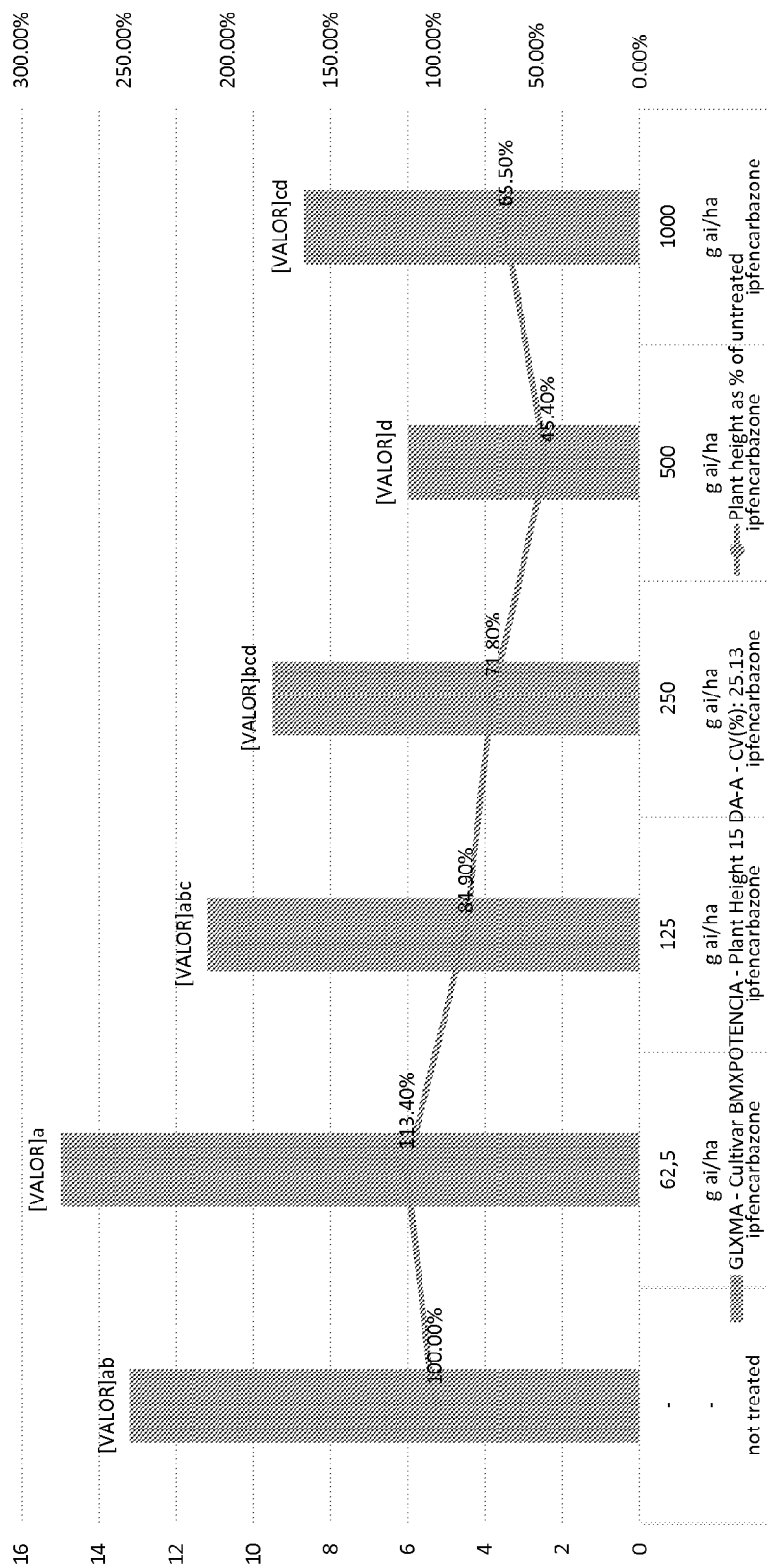
Figure 27:
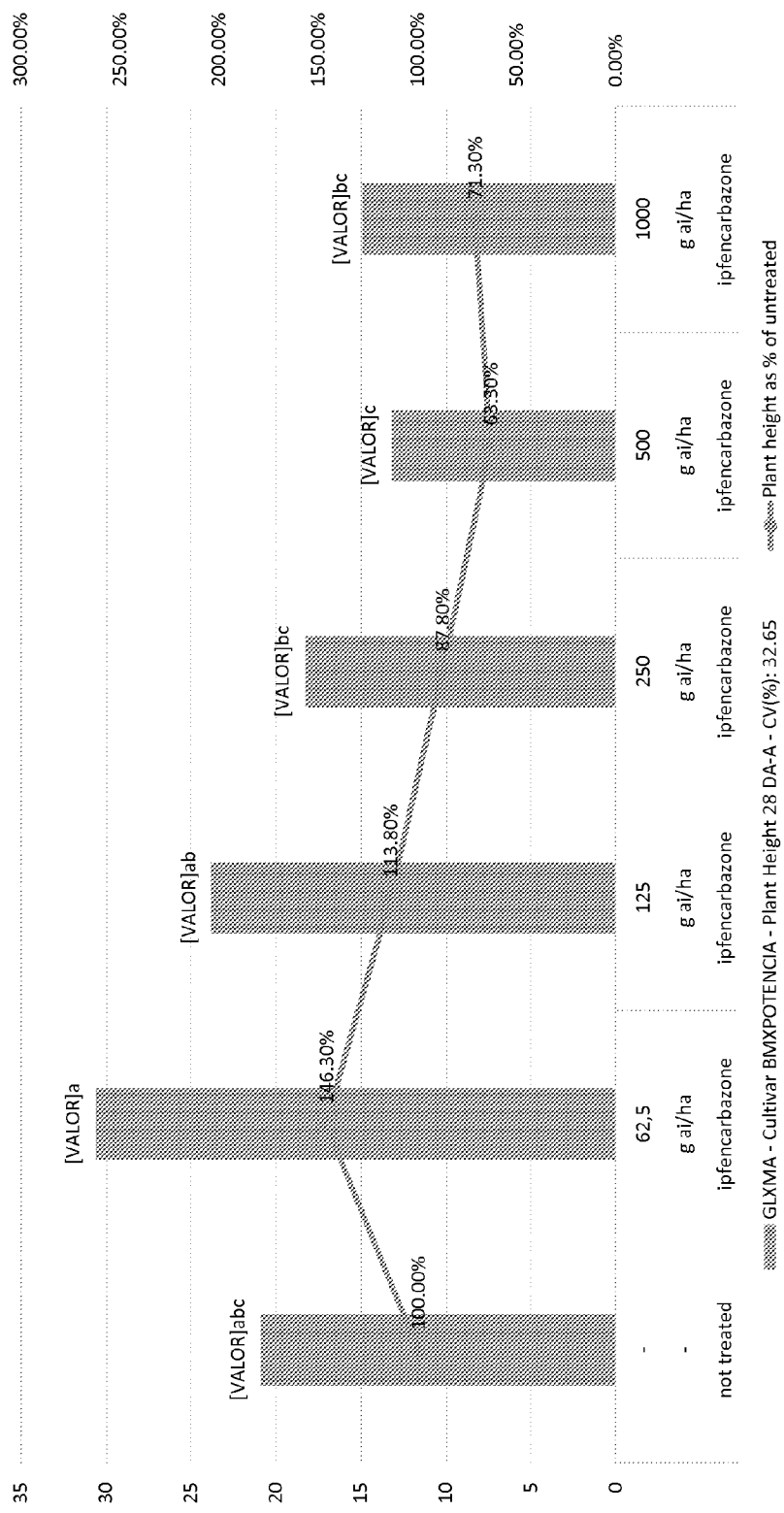
Figure 28:
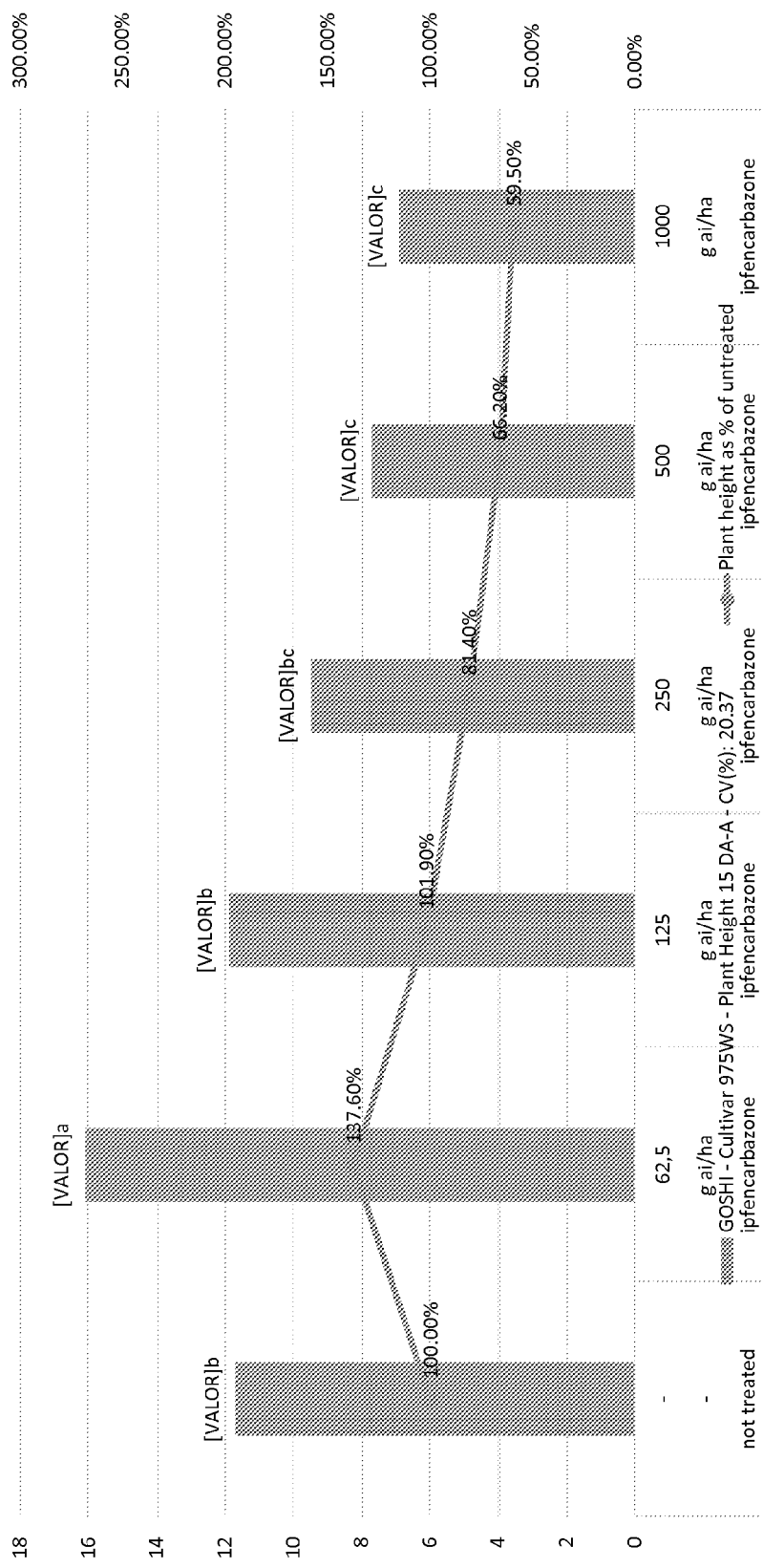
Figure 29:
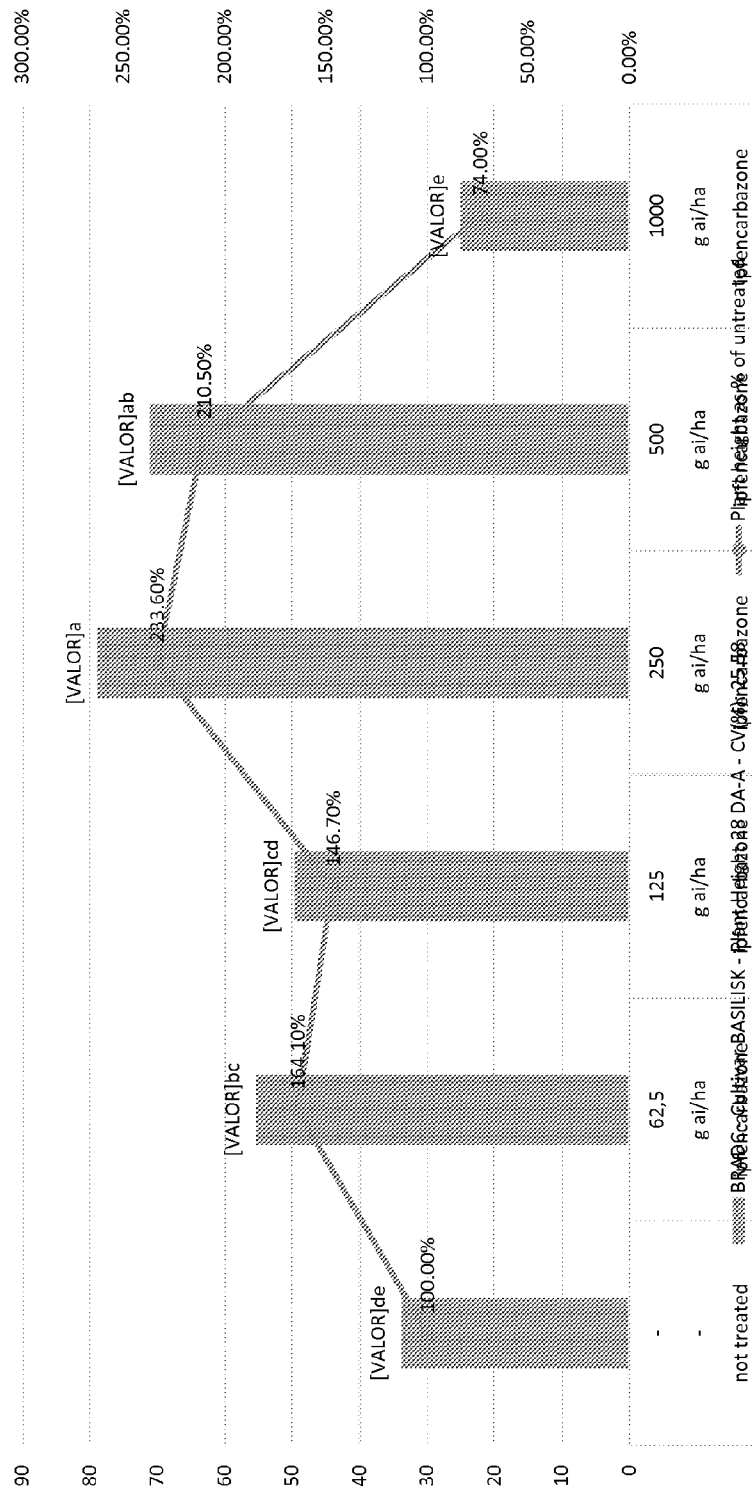
Figure 30:
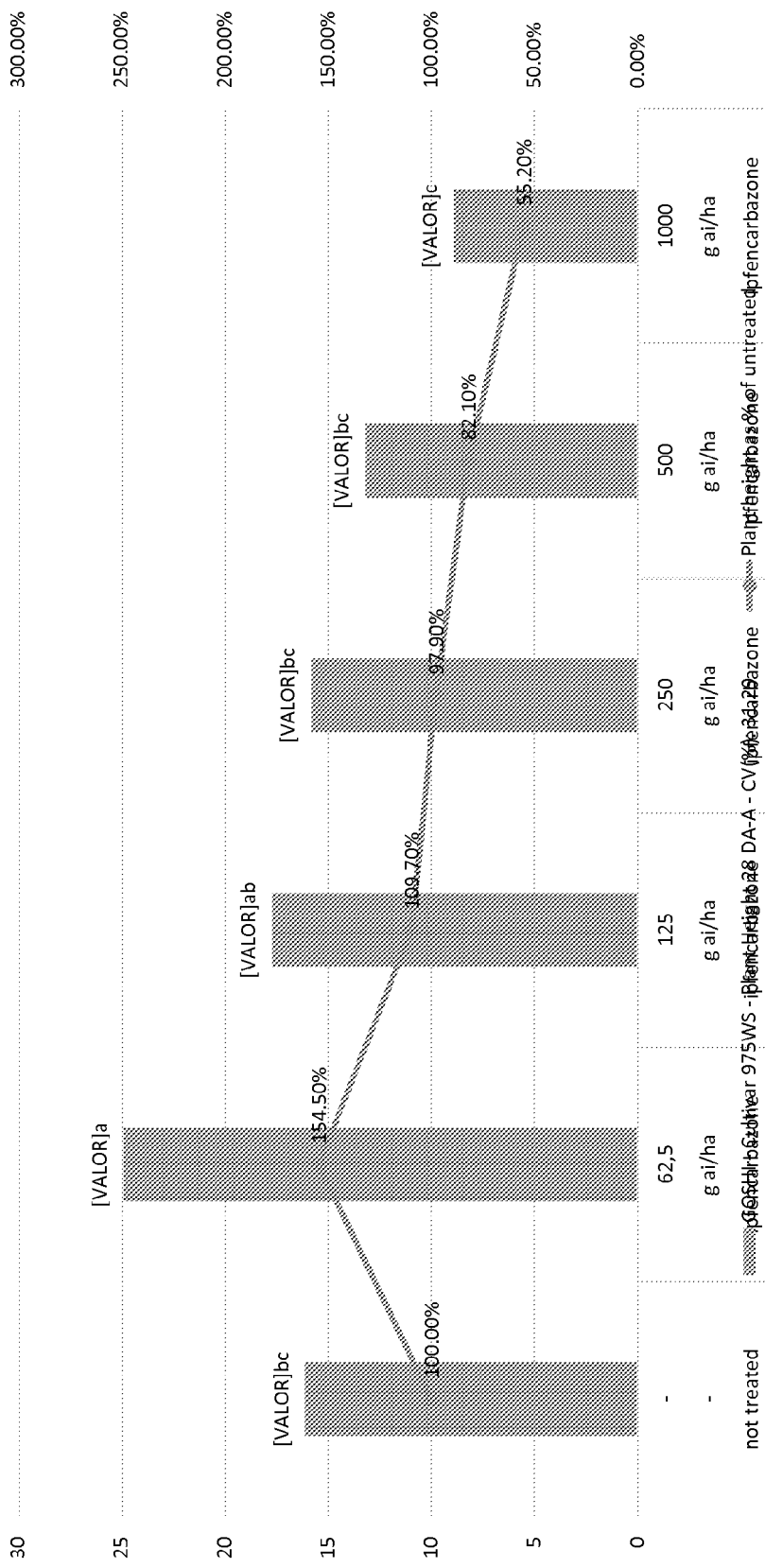
Figure 31:
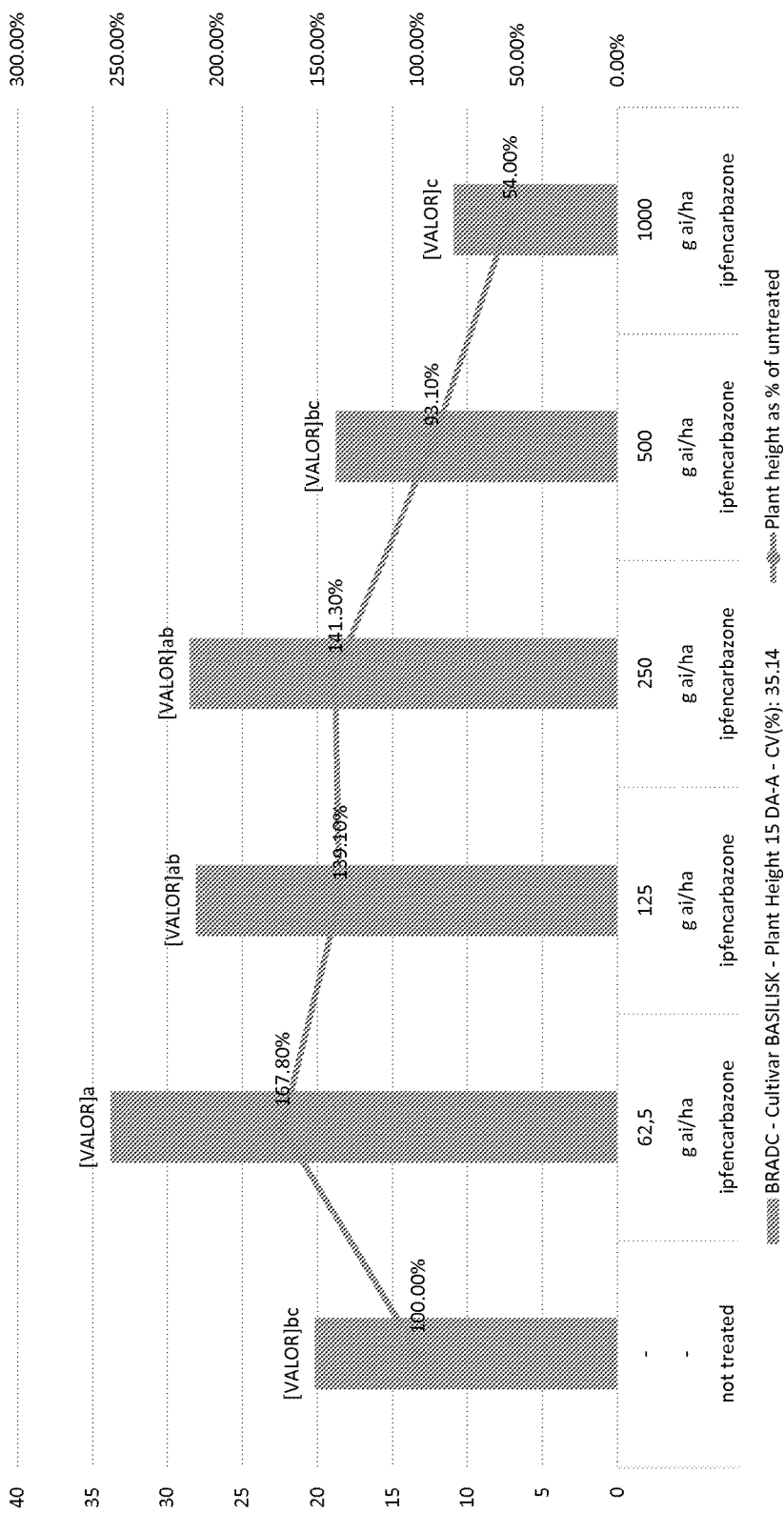

FIG. 11 shows photographs of trays containing multiple plant species that were either test plants in an untreated control or treated with varying amounts of ipfencarbazone in grams of active ingredient per hectare; 1—DIGNU: *Digitaria nuda*; 2—ELEIN: *Eleusine indica*; 3—LOLMU: *Lolium multiflorum*; 4—TRZAX01: wheat cultivar Itaipú; 5—TRZAX02: wheat cultivar Iguaçú; 6—TRZAX03: wheat cultivar BRS327; 7—SORVU: *Sorghum bicolor*; 8—ZEAMX: corn; 9—PHSVX: dry bean; 10—GLXMA: soybean; 11—GOSHI: cotton; 12—HELAN: sunflower; 13—ECHCG: *Echinochloa crus-galli*; 14—ECGCO: *Echinochloa colona*; 15—SETGE: *Setaria geniculata*; 16—BRADC: *Brachiaria decumbens*; 17—BRAPL: *Brachiaria plantaginea*; 18—SORHA: *Sorghum halepense*; 19—CCHEC: *Cenchrus echinatus*; 20—BIDPI: *Bidens pilosa*; 21—RAPSR: *Raphanus sativus*; 22—CASOB: *Cassia obtusifolia*; 23—EPHHL: *Euphorbia heterophylla*; 24—IAQGR: *Ipomoea grandifolia*; 25—AMAVI: *Amaranthus viridis*;

FIG. 12 shows photographs of trays containing multiple plant species that were either test plants in an untreated control or treated with varying amounts of ipfencarbazone in grams of active ingredient per hectare; DIGNU: *Digitaria nuda*; ELEIN: *Eleusine indica*; LOLMU: *Lolium multiflorum*; TRZAX01: wheat cultivar Itaipú; TRZAX02: wheat cultivar Iguaçú; TRZAX03: wheat cultivar BRS327; SORVU: *Sorghum bicolor*; ZEAMX: corn; PHSVX: dry bean; GLXMA: soybean; GOSHI: cotton; HELAN: sunflower;

FIG. 13 shows photographs of trays containing multiple plant species that were either test plants in an untreated control or treated with varying amounts of ipfencarbazone in grams of active ingredient per hectare; ECHCG: *Echinochloa crus-galli*; ECGCO: *Echinochloa colona*; SETGE: *Setaria geniculata*; BRADC: *Brachiaria decumbens*; BRAPL: *Brachiaria plantaginea*; SORHA: *Sorghum halepense*; CCHEC: *Cenchrus echinatus*; BIDPI: *Bidens pilosa*; RAPSR: *Raphanus sativus*; CASOB: *Cassia obtusifolia*; EPHHL: *Euphorbia heterophylla*; IAQGR: *Ipomoea grandifolia*; AMAVI: *Amaranthus viridis*;

FIG. 14 shows a graph of plant height and percent increase over the untreated control as a function of ipfencarbazone concentration for TRZAX: *Triticum aestivum*, cultivar Itaipú at 15 days after application;

FIG. 15 shows a graph of plant height and percent increase over the untreated control as a function of ipfencarbazone concentration for TRZAX: *Triticum aestivum*, cultivar Itaipú at 28 days after application;

FIG. 16 shows a graph of plant height and percent increase over the untreated control as a function of ipfencarbazone concentration for TRZAX: *Triticum aestivum*, cultivar Iguaçú at 15 days after application;

FIG. 17 shows a graph of plant height and percent increase over the untreated control as a function of ipfencarbazone concentration for TRZAX: *Triticum aestivum*, cultivar Iguaçú at 28 days after application;

FIG. 18 shows a graph of plant height and percent increase over untreated control as a function of ipfencarbazone concentration for TRZAX: *Triticum aestivum*, cultivar BRS327 at 15 days after application;

FIG. 19 shows a graph of plant height and percent increase over untreated control as a function of ipfencarbazone concentration for TRZAX: *Triticum aestivum*, cultivar BRS327 at 28 days after application;

FIG. 20 shows a graph of plant height and percent increase over untreated control as a function of ipfencarbazone concentration for SORVU: *Sorghum bicolor* at 15 days after application;

FIG. 21 shows a graph of plant height and percent increase over untreated control as a function of ipfencarbazone concentration for SORVU: *Sorghum bicolor* at 28 days after application;

FIG. 22 shows a graph of plant height and percent increase over untreated control as a function of ipfencarbazone concentration for ZEAMX: *Zea mays* at 15 days after application;

FIG. 23 shows a graph of plant height and percent increase over untreated control as a function of ipfencarbazone concentration for ZEAMX: *Zea mays* at 28 days after application;

FIG. 24 shows a graph of plant height and percent increase over untreated control as a function of ipfencarbazone concentration for PHSVX: *Phaseolus vulgaris* at 15 days after application;

FIG. 25 shows a graph of plant height and percent increase over untreated control as a function of ipfencarbazone concentration for PHSVX: *Phaseolus vulgaris* at 28 days after application;

FIG. 26 shows a graph of plant height and percent increase over untreated control as a function of ipfencarbazone concentration for GLXMA: *Glycine max* at 15 days after application;

FIG. 27 shows a graph of plant height and percent increase over untreated control as a function of ipfencarbazone concentration for GLXMA: *Glycine max* at 28 days after application;

FIG. 28 shows a graph of plant height and percent increase over untreated control as a function of ipfencarbazone concentration for GOSHI: *Gossypium hirsutum* at 15 days after application;

FIG. 29 shows a graph of plant height and percent increase over untreated control as a function of ipfencarbazone concentration for BRADC: *Brachiaria decumbens* at 28 days after application;

FIG. 30 shows a graph of plant height and percent increase over untreated control as a function of ipfencarbazone concentration for GOSHI: *Gossypium hirsutum* at 28 days after application;

FIG. 31 shows a graph of plant height and percent increase over untreated control as a function of ipfencarbazone concentration for BRADC: *Brachiaria decumbens* at 28 days after application.

DETAILED DESCRIPTION

Ipfencarbazone is classified as a tetrazolinone compound with a mode of action characterized by impacting cell division in the plant via inhibition of very long chain fatty acids (VLCFA's). Other classes of compounds that share this activity include acetamides, chloracetamides, and oxyacetamides.

Ipfencarbazone is safe for use on monocotyledonous crops including rice, corn, *sorghum*, millet, wheat, barley, oats, rye and triticale. As disclosed herein, at a range of rates there was a significant visible effect that suggested stimulation of a range of both monocotyledon and dicotyledon based crops, including corn, wheat, triticale, soybeans, dry beans, cotton, and the like.

Embodiments herein relate to the use of ipfencarbazone as a biostimulant (or plant growth regulator) for inter alia corn, wheat, soybeans, dry beans, cotton and pasture grasses when applied to the crop at specified application rates. This effect is particularly pronounced when applied post-emergence. Thus, certain application rates of ipfencarbazone, applied post emergent to a crop, demonstrated a significant increase in growth rate including, for example, biomass, leaf area, and plant height across a range of crop types.

As used herein, "plant" embraces plant crops (or just crops), ornamentals, trees, grasses, annuals, perennials or any other commonly cultivated member of the kingdom Plantae.

The application rate addition of ipfencarbazone may bolster the initial growth of seeds and/or crop seedlings, with the potential of masking phytotoxic effects of other agents when used in combinations and improve the initial plant stand. Other effects may include better plant health and more uniform stand through, for example, decreased seedling loss.

In particular embodiments, low application rates of ipfencarbazone, such as about 60 to about 125 grams per hectare, of ipfencarbazone demonstrated a positive effect on crop plants such as corn, wheat, soybean and dry bean seedlings, stimulating growth. Increased biomass, leaf area and rate of growth of crop plants were also observed. The methods herein may complement the spectrum of weed control and may be combined with other biostimulants/plant growth regulators (seed treatment) in a starter kit. These and other advantages will be apparent to those skilled in the art.

In some embodiments, there are provided methods comprising applying to a crop plant a composition comprising ipfencarbazone in an amount sufficient to stimulate plant growth. The term "crop plant(s)" as used herein, includes any edible or non-edible plant, including decorative, plant species with commercial value, which is planted and cultivated for commercial use. Thus, crop plants include floral and non-floral plants, perennials and annuals, trees, shrubs, vegetable plants, fruit trees, turf, and ground cover. Non-limiting specific examples of crop plants include canola, flax, peas, lentils, beans, linola, mustard, chickpeas, sunflowers, potatoes, seedling alfalfa, onions, soybeans and turf grass. The term "plants" is meant to include germinant seeds, cuttings, emerging seedlings, and established vegetation, including roots and above-ground portions, for example, leaves, stalks, flowers, fruits, branches, limbs, root, and the like.

The term "turf" used herein refers to grass which grow in areas in which they are desired, or purposely planned for and maintained, for example, a lawn. Turf also refers to a sod, where the surface layer of ground consisting of a mat of grass and grass roots.

The term "an amount of sufficient to stimulate or promote plant growth" means any amount of ipfencarbazone capable of increasing seedling germination, plant height, biomass, enhancing color, and the like, relative to an untreated control. In general, the amount sufficient to stimulate plant growth may be within the application rate range of from about 1 to about 1,000 grams of ipfencarbazone (active ingredient, a.i.) per hectare (ha). Optimal application rates for enhancing/stimulating plant growth may depend on a given crop plant and the ideal application rate range may comprise any sub-range from about 1 to about 1,000 grams ipfencarbazone per hectare, such as from about 50 to about 125 g a.i./ha, or 60 to 250 g a.i./ha, including any smaller or larger sub-ranges thereof, such as about 1 to about 60 g a.i./ha or about 250 to about 1,000 g a.i./ha.

In some embodiments, the amount sufficient to stimulate plant growth is in a range from about 20 grams per hectare to about 1,000 grams per hectare. In some embodiments, the amount sufficient to stimulate or promote plant growth is in a range from about 50 grams per hectare to about 250 grams per hectare. In some embodiments, the amount sufficient to stimulate plant growth is in a range from about 60 grams per hectare to about 125 grams per hectare, or about 1 gram per hectare to about 60 grams per hectare. As indicated in the Examples below and in the Figures, the particular applications rates that may be useful are readily determined based on a particular target crop.

In some embodiments, stimulating or promoting plant growth is assessed by enhanced seedling germination, plant height, leaf area, biomass, plant vigor, plant color, or combinations thereof. One or more of these characteristics can be measured by conventional means. Others may be assessed by visual observation.

In some embodiments, enhanced plant height is an increase in height from about 105 percent to about 400 percent of the control. In some embodiments, enhanced plant height is an increase in height from about 120 percent to about 350 percent of the control. As demonstrated in the Examples herein below, a series of application rates for a particular target crop plant can be used to determine a particular optimal application rate for a given plant, the optimal increase in characteristics being different depending on the exact crop plant.

In some embodiments, the applying step is carried out post-emergence. In some embodiments, post-emergence comprises seedling stage of the crop plant. In some embodiments, the applying step is carried out pre-emergence. In some embodiments, application of the compositions disclosed herein may be performed both pre- and post-emergence. In some embodiments, the applying step can be applied at any growth stage, including but not limited to, pre-emergence, early post emergence, and later stages of a crop growth cycle.

In some embodiments, compositions herein may be applied to perennial crops, including, without limitation, Stone fruits (cherries, plums, apricots, peaches, nectarines), blueberries, mangos, avocados, pastures, turfgrass, ornamentals, tree crops, eucalyptus, pine, tea, coffee, nut trees, citrus, tropical fruits, pome fruits, grapes and vines, perennial grasses, caneberries, bananas, sugarcane. In some embodiments, the crop plant is an upland crop. In some embodiments, the crop is selected from the group consisting of corn, wheat, soybean, dry bean, cotton, cereals, rice, maize, *sorghum*, sugar cane, canola, soya, turf, barley, potato, sweet potato, sunflower, rye, oats, sugar beet, safflower, alfalfa, cassava, cucurbits, pineapple and pastures. In some embodiments, any one or more of the foregoing crops may be specifically not treated or excluded. Desirable plants are generally referred to herein as "crop plants."

In some embodiments, the compositions employed to stimulate plant growth may further comprises a second active selected from the group consisting of 2,4-D, 2,4-DB, acetochlor, acifluorfen, alachlor, ametryn, amicarbazone, atrazine, aminopyralid, benefin, bensulfuron, bensulide, bentazon, bromacil, bromoxynil, butylate, carfentrazone, chlorimuron, chlorsulfuron, clethodim, clomazone, clopyralid, cloransulam, cycloate, DCPA, desmedipham, dicamba, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaben, isoxaflutole, lactofen, linuron, MCPA, MCPB, mesotrione, metolachlor-s, metribuzin, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, and triflusulfuron.

In particular embodiments, methods may employ combinations of ipfencarbazone in a tank mix with flucarbazone and/or amicarbazone, optionally with or without further plant growth (i.e., biostimulating) agents.

Methods disclosed herein employing ipfencarbazone as a biostimulant can be used in conjunction with a second active (separately or tank mixed with ipfencarbazone) that controls one or more grasses. Examples of grass plant species against which the compositions and methods can be used include, but are not limited to, the following: Barnyard grass (*Echinochloa crus-galli*), Bermudagrass (*Cynodon dactylon*), Broadleaf Signalgrass (*Brachiaria platyphylla*), Bromes (*Bromus* species), Crabgrass species (*Digitaria* species), Crowfootgrass (*Dactyloctenium aegyptium*), Fall *Panicum* (*Panicum dichotomiflorum*), Fescue (*Festuca arundinacea*), Foxtail Barley (*Hordeum jubatum*), Foxtail species (*Setaria* species), Goosegrass (*Eleusine indica*), Guineagrass (*Panicum maximum*), Itchgrass (*Rottboellia exaltata*), Junglerice (*Echinochloa colona*), Lovegrass (*Eragrostis cilanensis*), Orchardgrass (*Dactylis glomerata*), Perennial grasses, Quackgrass (*Agropyron repens*), Persian Darnel, Proso Millet, Red Rice (*Oryza sativa*), Johnsongrass rhizome (*Sorghum halepense*), Rye (*Secale cereale*), Rygrasses (*Lolium* species), Johnsongrass seedling (*Sorghum halepense*), Shattercane (*Sorghum bicolor*), Smooth Crabgrass, Southwestern Cupgrass (*Eriochlola gracillis*), Sprangetops (*Leptochloa* species), Texas *Panicum* (*Panicum texanum*), Volunteer Barley, Volunteer Oats, Volunteer Corn, Volunteer Canary Seed, Volunteer Wheat, Wheat (*Triticum aestivum*), Wild Oats (*Avena fatua*), Wild Proso Millet (*Panicum miliaceum*), Witchgrass (*Panicum capillare*), Woolly Cupgrass (*Eriochloa villosa*), Wirestem Muhly (*Muhlenbergia frondisa*), and Yellow Foxtail (*Setaria geniculata*—include). Monocotyledonous weeds include the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds include the genera: *Abutilon, Amaranthus, Ambrosia, Anoda, Anthemis, Aphanes, Atriplex, Beffis, Bidens, Capsella, Carduus, Cassia, Centaurea, Chenopodium, Cirsium, Convolvulus, Croton, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Merremia, Momordica, Mullugo, Myosotis, Papaver, Pharbitis, Plantago, Polygonum, Portulaca, Ranunculus, Raphanus, Ricinus, Rorippa, Rotala, Rumex, Salsola, Senecio, Sesbania, Sida, Sinapis, Solanum, Sonchus, Sphenoclea, Stellaria, Stizolobium, Taraxacum, Thlaspi, Trifolium, Urtica, Veronica, Viola, Xanthium.*

In some embodiments, the compositions employed in the methods herein may further comprise a surfactant. In some embodiments, the surfactant is a non-ionic surfactant. In further particular embodiments, the non-ionic surfactant is selected from the group consisting of ethoxylated fatty acids, alcohol ethoxylates, tristyrylphenol ethoxylates, ethoxylated sorbitan fatty acid esters or mixtures thereof. A surfactant may increase solubility of an active ingredient in a solution. A surfactant may also affect spray retention, droplet spreading, and dry rates. A surfactant may be anionic, cationic, non-ionic or amphoteric. Examples of anionic surfactants include phosphoric mono- and di-esters of long-chain alcohols having 14 to 22 carbon atoms and the salts thereof; phosphoric mono- and di-esters of alkylene oxide addition products of long-chain alcohols having 14 to 22 carbon atoms and the salts thereof; alkylsulfates having 14 to 22 carbon atoms; polyoxyethylene alkyl ether sulfates of alcohols having 14 to 22 carbon atoms; alkane sulfonates having 14 to 22 carbon atoms; and olefin sulfonates having 14 to 22 carbon atoms.

Suitable non-ionic surfactants include, for example, ethoxylated fatty acids, alcohol ethoxylates, tristyrylphenol ethoxylates, ethoxylated sorbitan fatty acid esters or mixtures thereof. Ethoxylated fatty acids include castor or canola oil ethoxylates having at least 25, or about 27 to 37 ethoxy units, such as Sunaptol CA350 (castor oil ethoxylate with 35 ethoxy units) of Uniqema (formerly ICI Surfactants), Mergital EL33 (castor oil ethoxylate with 33 ethoxy units) of Henkel KGaA, Eumulgin C03373 (canola oil ethoxylate with 30 ethoxy units) of Henkel KGaA and Ukanil 2507 (castor oil ethoxylate) of Uniqema.

Surfactants may be present in any desired amount. For example, a surfactant may be present in an amount of about 0.1 to about 30% by weight in the formulation. In a particular embodiment, a surfactant is present in an amount of about 1 to about 9% by weight in the formulation. In another embodiment, a surfactant is present in an amount of about 10 to about 20% by weight in the formulation.

An emulsifier is a type of surfactant typically used to maintain dispersion. Non-limiting examples of emulsifiers include Agent 2201-76, Agent 2416-20, Emulpon CO-360, T-Det C-40®, and Agnique™ SBO-10. Agent 2201-76 is manufactured by Stepan Company (22 W. Frontage Road, Northfield, Ill.), which is a blend of nonionic and anionic surfactants (82%). The ingredients in Agent 2201-76 are alkylbenzene sulfonate and fatty acid ethoxylate, aromatic petroleum hydrocarbon, 1-hexanol and naphthalene. Agent 2416-20 is also manufactured by Stepan Company (22 W. Frontage Road, Northfield, Ill.), which is a blend of nonionic and anionic surfactants (35-37%). Agent 2416-20 also includes aromatic petroleum hydrocarbon (57-58%), and naphthalene (6-7%). Emulpon CO-360 is manufactured by Akzo Nobel Chemicals Ltd. (525 West Van Buren, Chicago, Ill.), which contains ethoxylated castor oil (100% by weight) and oxirane (<0.001% by weight). T-Det C-40® may be purchased from Harcros Organics (5200 Speaker Road., P.O. Box 2930, Kansas City, Kans.), or from Akzo Nobel Chemicals Ltd. (525 West Van Buren, Chicago, Ill.), which is a non-ionic emulsifier, and a brand of ethoxylated (polyethoxylated) castor oil. Agnique™ SBO-10 is manufactured by Cognix GmbH headquartered in Monheim, Germany, which contains alkoxylated triglycerides as an ethoxylated soybean oil.

A crop oil, or a crop oil concentrate, may be added, for example, in order to increase the efficacy of a formulation including ipfencarbazone. Although not wishing to be bound by any particular theory, a crop oil is believed to keep the leaf surface moist longer than water, which in turn allows more time for ipfencarbazone to penetrate, thereby increasing the amount of ipfencarbazone that will enter the plant (e.g. weed or crop). A crop oil can improve uptake of ipfencarbazone by plant (e.g. weed or crop). A crop oil can therefore improve, enhance, increase or promote efficacy or activity. Crop oils may contained from 1% to 40% by weight, or 1% to 20% by weight in the formulation. A crop oil can be derived from either petroleum oil or vegetable oil. Non-limiting examples of crop oil include soybean oils and petroleum based oils.

The compositions employed in the methods herein can be in customary formulations. Non-limiting examples include solutions, emulsions, suspensions, wettable powders, powders, dusts, pastes, soluble powders, granules, pellets, emulsifiable concentrate, oil spray, aerosol, natural and synthetic materials impregnated with active compound, and very fine capsules (e.g. in polymeric substances). In certain embodiments, the composition is in a form of an emulsifiable concentrate, wettable powder, granule, dust, oil spray or aerosol.

The compositions may optionally include adherent coatings. Such coatings include those that aid the active ingredient to adhere to the intended environment, for example, a crop plant. Adherent coatings include carboxymethylcellulose, natural and synthetic polymers in various forms, such as powders, granules or latexes. Other adherent coatings include gum arabic, polyvinyl alcohol and polyvinyl acetate. Phospholipids, such as cephalins and lecithins, and synthetic phospholipids are also examples of adherent coatings. Further additives may be mineral and vegetable oils.

Colorants can also be included in the formulations. Non-limiting examples are inorganic pigments, such as iron oxide, titanium oxide and Prussian Blue, and organic dye-stuffs, such as alizarin dyestuffs, azo dye-stuffs and metal phthalocyanine dyestuffs, and trace nutrients such as salts of iron, manganese, boron, copper, cobalt, molybdenum and zinc.

Compositions can be applied in the form of ready mixes. Ipfencarbazone can also be formulated individually and mixed upon use, i.e. applied in the form of tank mixes. Ipfencarbazone can be used as such or in the form of their formulations, and furthermore also as mixtures with plant growth stimulants, ready mixes or tank mixes. Compositions may also be mixed with other active compounds, such as herbicides, fungicides, insecticides, acaricides, nematicides, bird repellents, growth substances, plant nutrients and agents which improve soil structure. For particular application purposes, in particular when applied post-emergence, formulations such as mineral or vegetable oils which are tolerated by plants (for example the commercial product "Oleo DuPont 11E") or ammonium salts such as, for example, ammonium sulphate or ammonium thiocyanate, as further additives can be included.

Ipfencarbazone compositions disclosed herein may also exclude any of the aforementioned. For example, herbicides, fungicides, insecticides, acaricides, nematicides, bird repellents, growth substances, plant nutrients and agents which improve soil structure can be excluded or omitted from a composition or method disclosed herein.

Compositions can be used as such, in the form of their formulations or in the forms prepared therefrom by dilution of a concentrated form, such as ready-to-use or concentrated liquids, solutions, suspensions, emulsions, or solids, such as, powders, pastes, granules and pellets. They are dispersed in the customary manner, for example by watering, spraying, atomizing, dusting or scattering.

Compositions can be produced by mixing or suspending one of, an active ingredient, and optionally a stabilizer, an adjuvant, a diluent or a solvent. In certain embodiments, formulations disclosed herein can be produced, for example by first mixing or suspending one or more stabilizers with a diluent or solvent. Next, the appropriate amount of adjuvants is combined to the resulting mixture containing the stabilizers. An active ingredient, ipfencarbazone, can added at any time, such as at the end, and blended until the formulation becomes mostly or entirely homogeneous.

In particular embodiments, a composition may comprise a second plant growth stimulant. In some embodiments, the plant growth stimulant is selected from the group consisting of ancymidol, butralin, alcohols, chlormequat chloride, cytokinin, daminozide, ethephon, ethylene, flurprimidol, gibberellic acid, gibberellin mixtures, indole-3-butyric acid (IBA), maleic hydrazide, potassium salt, mefluidide, mepiquat chloride, mepiquat pentaborate, naphthalene-acetic acid (NAA), 1-naphthaleneacetamide (NAD), n-decanol, paclobutrazol, prohexadione calcium, trinexapac-ethyl, and uniconazole. Other stimulants include those sold under the trade names BIOZYME® (comprising natural plant extracts, manganese, sulfur, magnesium, boron, iron zinc), PILATUS® (comprising vegetal origin extracts, fulvic acid, inositol, zinc), ATONIK® (comprising p-Sodium Nitrophenolate, o-Sodium Nitrophenolate, 5-Sodium Nitroguaiacolate), Tytanit (comprising magnesium oxide, sulfur trioxide, complexed titanium), DELSOL™ (comprising Natural occurring plant growth rhizobacteria), BM86 (comprising aminoalcohol), HeadSet (comprising seaweed based fertilizer, magnesium nitrate), FOLTRON® (comprising nitrogen, phosphorus, potassium, iron, zinc, magnesium, manganese, boron, copper, molybdemum, Folcisteine), POLIQUEL® (comprising magnesium oxide, sulfur, iron, manganese, zinc), and Podset.

In some embodiments, the composition is provided as a concentrate (e.g., suspension concentrate) and a diluting step is performed prior to the applying step thereby providing a diluted composition. In further embodiments, the applying step comprises spraying the diluted composition. Thus, in various embodiments, the composition comprises a diluent. In particular embodiments, the diluent is selected from the group consisting of water, an aliphatic hydrocarbon, an aromatic hydrocarbon, or an alkyl ester. The amount of diluent in a composition may range from 1% to 99%, or from 30% to 80%. Suitable diluents include, for example, a non-polar water-immiscible solvent, or a polar aprotic water miscible organic solvent. Non-polar solvents include, for example, substituted or unsubstituted aliphatic or aromatic hydrocarbons and esters of plant oils or mixtures thereof. Non-limiting examples of aromatic hydrocarbons include benzene or substituted benzene derivatives such as toluene, xylene, 1,2,4-trimethylbenzene, naphthalene or mixtures thereof. In a more particular embodiment, a solvent includes a mixture of napthalen and 1,2,4-trimethylbenzene. In another more particular embodiment, a solvent is Aromatic 150, a heavy aromatic naptha solvent containing <10% naphthalene and <1.7% 1,2,4-trimethylbenzene.

Alkyl esters can also be used as non-polar, water immiscible diluents. Plant oils may be esterified with various alcohols to form alkyl esters of plant oils. Fatty acids of these plant oils have 5 to 20, or 6 to 15 carbon atoms. Alkyl esters of plant oils include, without limitation, methyl, ethyl and butyl esters of canola (*Brassica napus*), linseed, safflower (*Carthamus tinctorius* L.), soybean and sunflower oils. In one embodiment, the solvent is a mixture of methyl esters. A specific non-limiting example of methyl esters is Agent 2416-21 manufactured by Stepan Company (22 W. Frontage Road, Northfield, Ill.).

Water-miscible polar aprotic solvents include, for example, alkyl lactates, isopropyl lactate, alkyl carbonates, polyethylene glycols, polyethylene glycol alkyl ethers, polypropylene glycols, and polypropylene glycol alkyl ethers, or mixtures thereof.

The composition may optionally include one or more adjuvants. An adjuvant may enhance or improve herbicidal and/or plant growth performance, for example. Adjuvants may be added to the composition at the time of formulation, or by the applicator to a mix prior to treatment. Adjuvants include, for example, surfactants (emulsifier), crop oil, fertilizers, dispersing agents, compatibility agents, foaming activators, foam suppressants, correctives, and spray colorants (dyes). Nonlimiting adjuvants include Crop Oil Concentrate (COC), Methylated Seed Oil, also M. Soybean Oil (MSO), Organo-siliconates, Non Ionic Surfactants (NIS), and Methylated Vegetable Oil Concentrate (MVOC) An adjuvant may be present in any desired amount. For example, a formulation may contain 1% to 3% adjuvant, 3% to 8% of adjuvant, 8% to 16% adjuvant, 17% to 30% adjuvant, or 30% or (e.g. 40% or more) more adjuvant.

In some embodiments, a concentration of ipfencarbazone in the composition is in a range from about 1 percent by weight of the composition to about 80 percent by weight of the composition. In other embodiments, ipfencarbazone is in a range of about 5 percent to about 60 percent by weight of the composition.

In various embodiments, there are provided methods for stimulating plant growth in a crop plant. In a particular embodiment, a method includes applying, post emergence, a composition comprising about 60 grams per hectare to about 125 grams per hectare of ipfencarbazone and optionally a non-ionic surfactant.

In various embodiments, the non-ionic surfactant is selected from the group consisting of ethoxylated fatty acids, alcohol ethoxylates, tristyrylphenol ethoxylates, ethoxylated sorbitan fatty acid esters or mixtures thereof.

In further embodiments, there are provided concentrates for use with a crop plant comprising ipfencarbazone and a non-ionic surfactant, such that when diluted for application the amount of ipfencarbazone delivered is in a range from about 60 grams per hectare to about 125 grams per hectare in a single application.

As used herein, the singular forms "a", "and," and "the" include plural referents unless the context clearly indicates otherwise.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 90-100% includes 92.2% to 97.5%, 91.5 to 94.5, etc. Reference to a series of ranges, such as, overlapping ranges between 0.1% and 15%, and between 1% and 10%, include ranges between 0.1% and 1%, 0.1% and 10%, 1% and 15%, and 10% and 15%.

Embodiments herein are generally disclosed herein using affirmative language to describe the numerous embodiments. The disclosure also specifically includes embodiments in which particular subject matter is excluded, in full or in part, such as substances or materials, method steps and conditions, protocols, procedures, assays or analysis. Thus, even though the embodiments are generally not expressed herein in terms of what the invention does not include aspects that are not expressly included are nevertheless disclosed herein.

The following Examples are being submitted to illustrate embodiments of the invention. These Examples are intended to be illustrative only and are not intended to limit the scope of the invention. Also, parts and percentages are by weight unless otherwise indicated. As used herein, "room temperature" refers to a temperature of from about 20° C. to about 25° C.

EXAMPLES

The original objective of this Example was to evaluate the herbicidal effect of ipfencarbazone when applied as a post emergent treatment to a range of selected crops and weeds. Unexpectedly, crop plant growth stimulation was observed. The actual species of weeds and crops are listed in the summary data tabulated below and in FIGS. 1-13. By convention each plant species has a Bayer code (5-letter name) with the scientific name for the plant referenced in FIGS. 1-13. In each Figure, each tray contains the same configuration of weeds and/or crops. In each Figure there is one replication of each treatment (six treatments in total). The top three photographs in each Figure show the Bayer Codes and bottom three photographs are aligned with the top three facilitating viewing of the same plant species. Throughout the Examples various abbreviations as conventional shorthand notation and will be appreciated by those skilled in the art. Some exemplary abbreviations include, "CV"=Co-efficient of Variation," "LSD"=Least Significant Difference" (G/L (gram per L) AND GA/L (gram of active ingredient per L); "SC"=suspension concentrate formulation. The diluent in all treatments was water. By convention factors that are identical in all treatments (e.g. diluent and surfactant) are not listed in each treatment.

Figure 1:
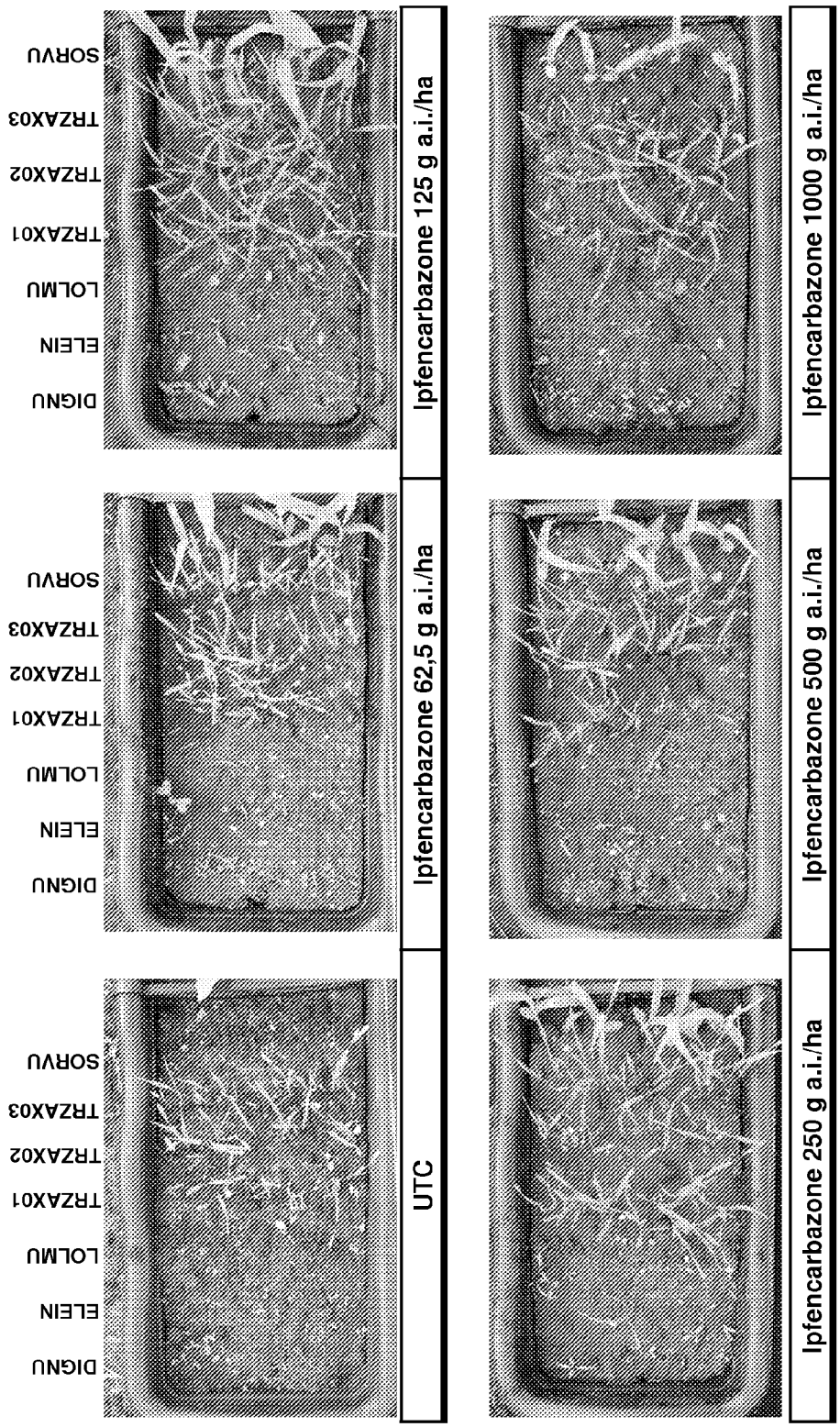
FIG. 1 shows photographs of trays containing multiple plant species that were either test plants in an untreated control or treated with varying amounts of ipfencarbazone in grams of active ingredient per hectare; DIGNU: *Digitaria nuda*; ELEIN: *Eleusine indica*; LOLMU: *Lolium multiflorum*; TRZAX01: wheat cultivar Itaipú; TRZAX02: wheat cultivar Iguaçú; TRZAX03: wheat cultivar BRS327; SORVU: *Sorghum bicolor*.
Figure 2:
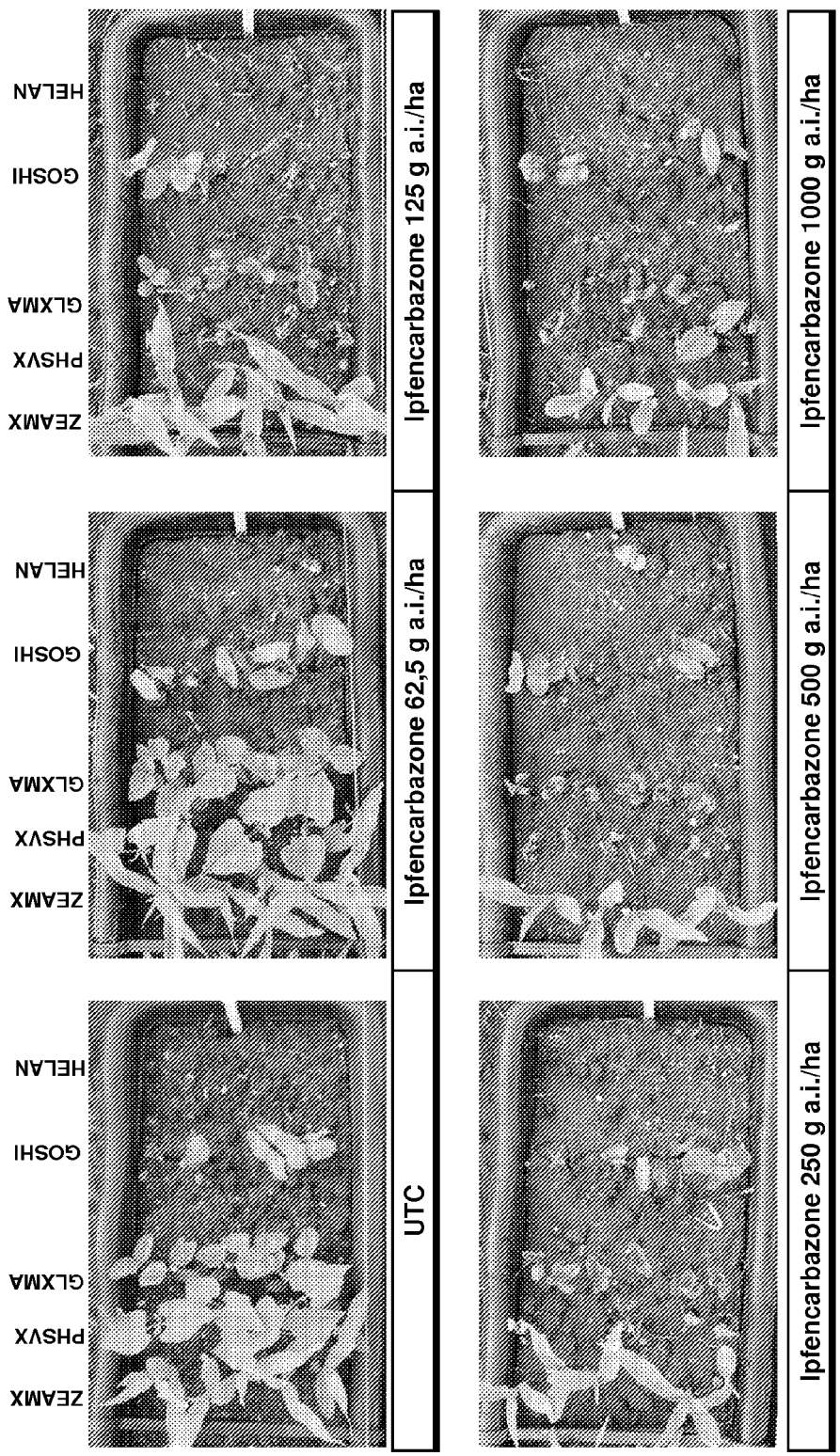
FIG. 2 shows photographs of trays containing multiple plant species that were either test plants in an untreated control or treated with varying amounts of ipfencarbazone in grams of active ingredient per hectare; ZEAMX: corn; PHSVX: dry bean; GLXMA: soybean; GOSHI: cotton; HELAN: sunflower.
Figure 3:
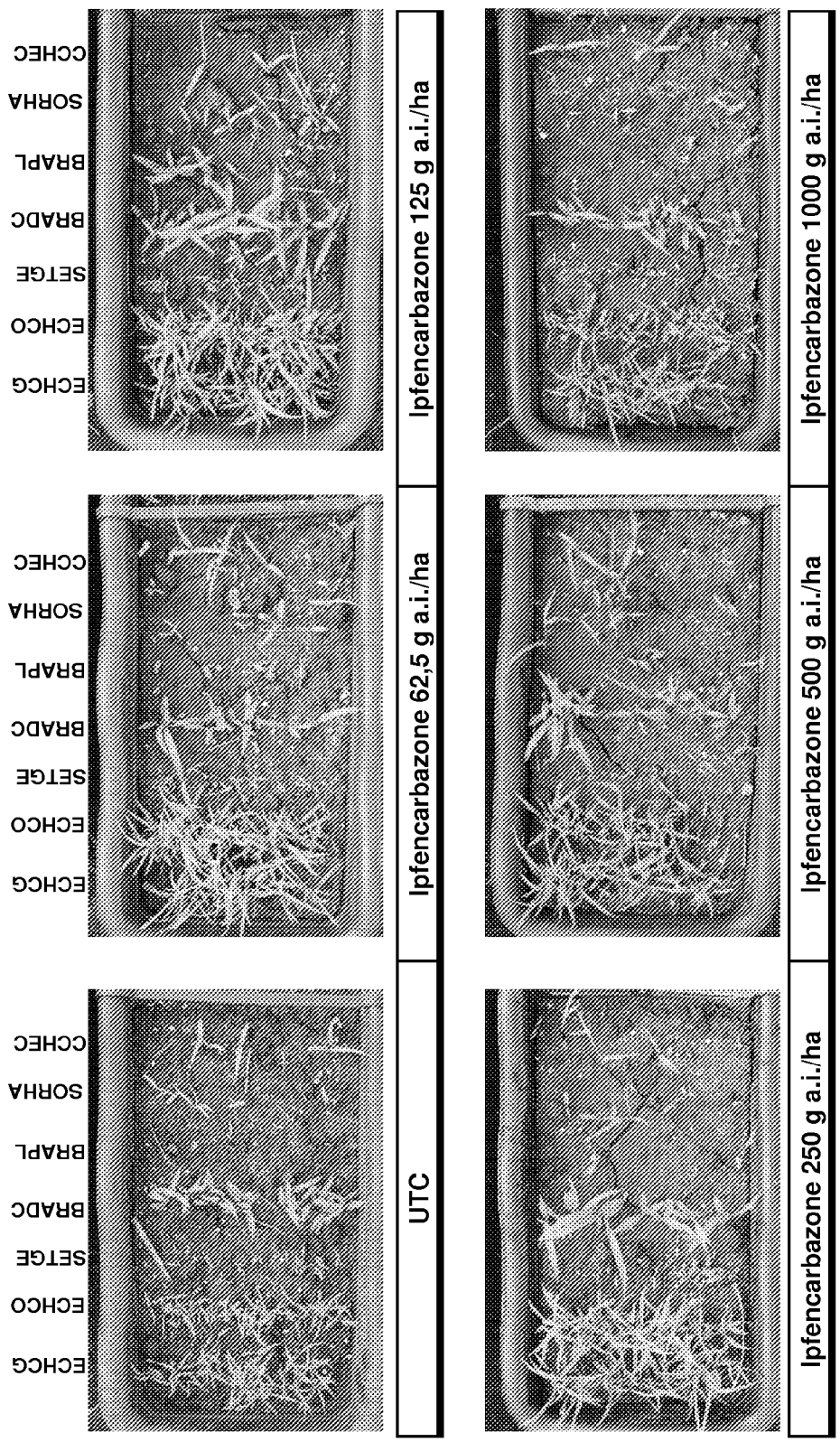
FIG. 3 shows photographs of trays containing multiple plant species that were either in an untreated control or treated with varying amounts of ipfencarbazone in grams of active ingredient per hectare; ECHCG: *Echinochloa crus-galli*; ECGCO: *Echinochloa colona*; SETGE: *Setaria geniculata*; BRADC: *Brachiaria decumbens*; BRAPL: *Brachiaria plantaginea*; SORHA: *Sorghum halepense*; CCHEC: *Cenchrus echinatus*.
Figure 4:
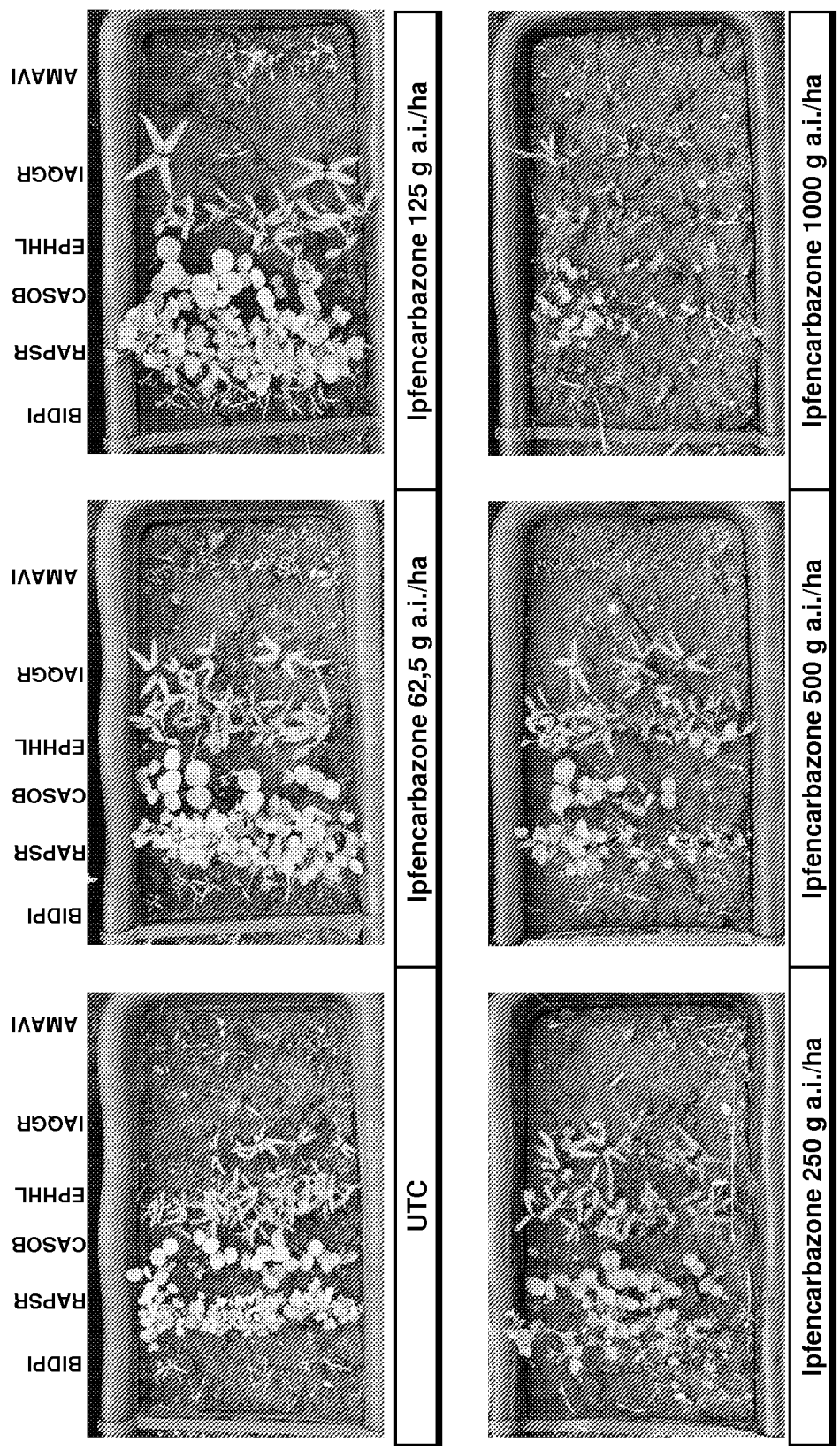
FIG. 4 shows photographs of trays containing multiple plant species that were either test plants in an untreated control or treated with varying amounts of ipfencarbazone in grams of active ingredient per hectare; BIDPI: *Bidens pilosa*; RAPSR: *Raphanus sativus*; CASOB: *Cassia obtusifolia*; EPHHL: *Euphorbia heterophylla*; IAQGR: *Ipomoea grandifolia*; AMAVI: *Amaranthus viridis*.
Figure 5:
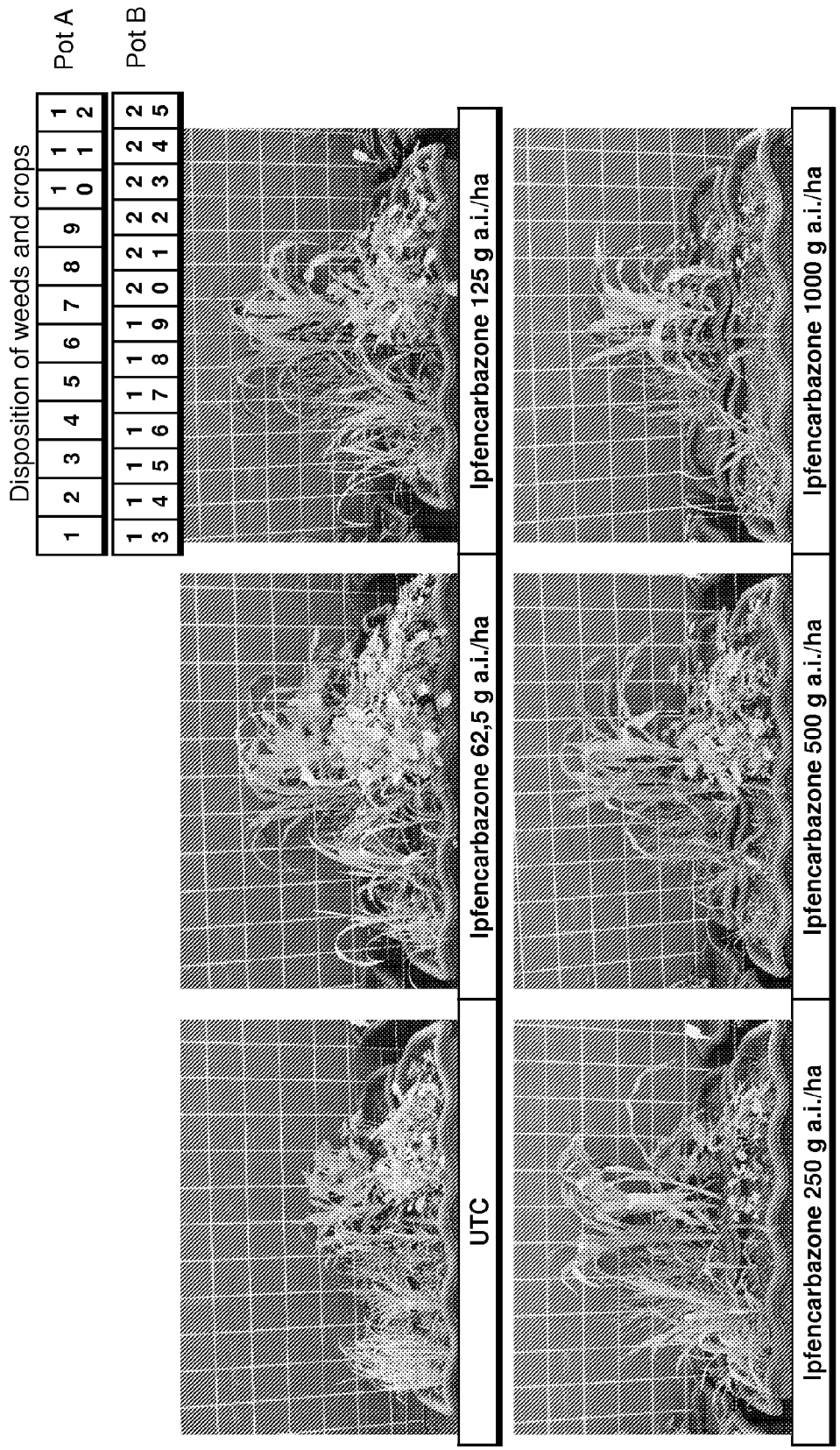
FIG. 5 shows photographs of trays containing multiple plant species that were either test plants in an untreated control or treated with varying amounts of ipfencarbazone in grams of active ingredient per hectare; 1—DIGNU: *Digitaria nuda*; 2—ELEIN: *Eleusine indica*; 3—LOLMU: *Lolium multiflorum*; 4—TRZAX01: wheat cultivar Itaipú; 5—TRZAX02: wheat cultivar Iguaçú; 6—TRZAX03: wheat cultivar BRS327; 7—SORVU: *Sorghum bicolor*; 8—ZEAMX: corn; 9—PHSVX: dry bean; 10—GLXMA: soybean; 11—GOSHI: cotton; 12—HELAN: sunflower; 13—ECHCG: *Echinochloa crus-galli*; 14—ECGCO: *Echinochloa colona*; 15—SETGE: *Setaria geniculata*; 16—BRADC: *Brachiaria decumbens*; 17—BRAPL: *Brachiaria plantaginea*; 18—SORHA: *Sorghum halepense*; 19—CCHEC: *Cenchrus echinatus*; 20—BIDPI: *Bidens pilosa*; 21—RAPSR: *Raphanus sativus*; 22—CASOB: *Cassia obtusifolia*; 23—EPHHL: *Euphorbia heterophylla*; 24—IAQGR: *Ipomoea grandifolia*; 25—AMAVI: *Amaranthus viridis*.
Figure 6:
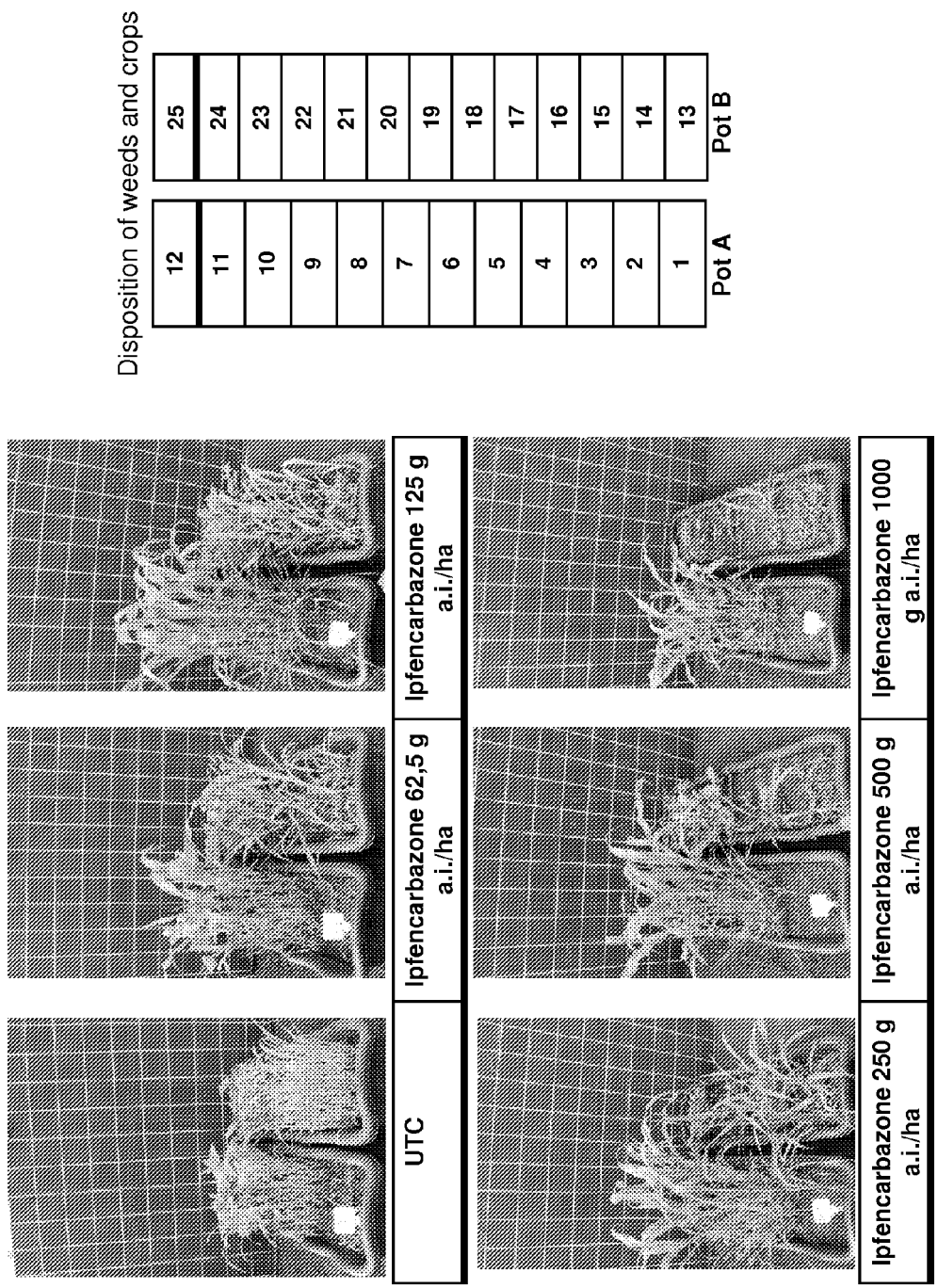
FIG. 6 shows photographs of trays containing multiple plant species that were either test plants in an untreated control or treated with varying amounts of ipfencarbazone in grams of active ingredient per hectare; 1—DIGNU: *Digitaria nuda*; 2—ELEIN: *Eleusine indica*; 3—LOLMU: *Lolium multiflorum*; 4—TRZAX01: wheat cultivar Itaipú; 5—TRZAX02: wheat cultivar Iguaçú; 6—TRZAX03: wheat cultivar BRS327; 7—SORVU: *Sorghum bicolor*; 8—ZEAMX: corn; 9—PHSVX: dry bean; 10—GLXMA: soybean; 11—GOSHI: cotton; 12—HELAN: sunflower; 13—ECHCG: *Echinochloa crus-galli*; 14—ECGCO: *Echinochloa colona*; 15—SETGE: *Setaria geniculata*; 16—BRADC: *Brachiaria decumbens*; 17—BRAPL: *Brachiaria plantaginea*; 18—SORHA: *Sorghum halepense*; 19—CCHEC: *Cenchrus echinatus*; 20—BIDPI: *Bidens pilosa*; 21—RAPSR: *Raphanus sativus*; 22—CASOB: *Cassia obtusifolia*; 23—EPHHL: *Euphorbia heterophylla*; 24—IAQGR: *Ipomoea grandifolia*; 25—AMAVI: *Amaranthus viridis*.
Figure 7:
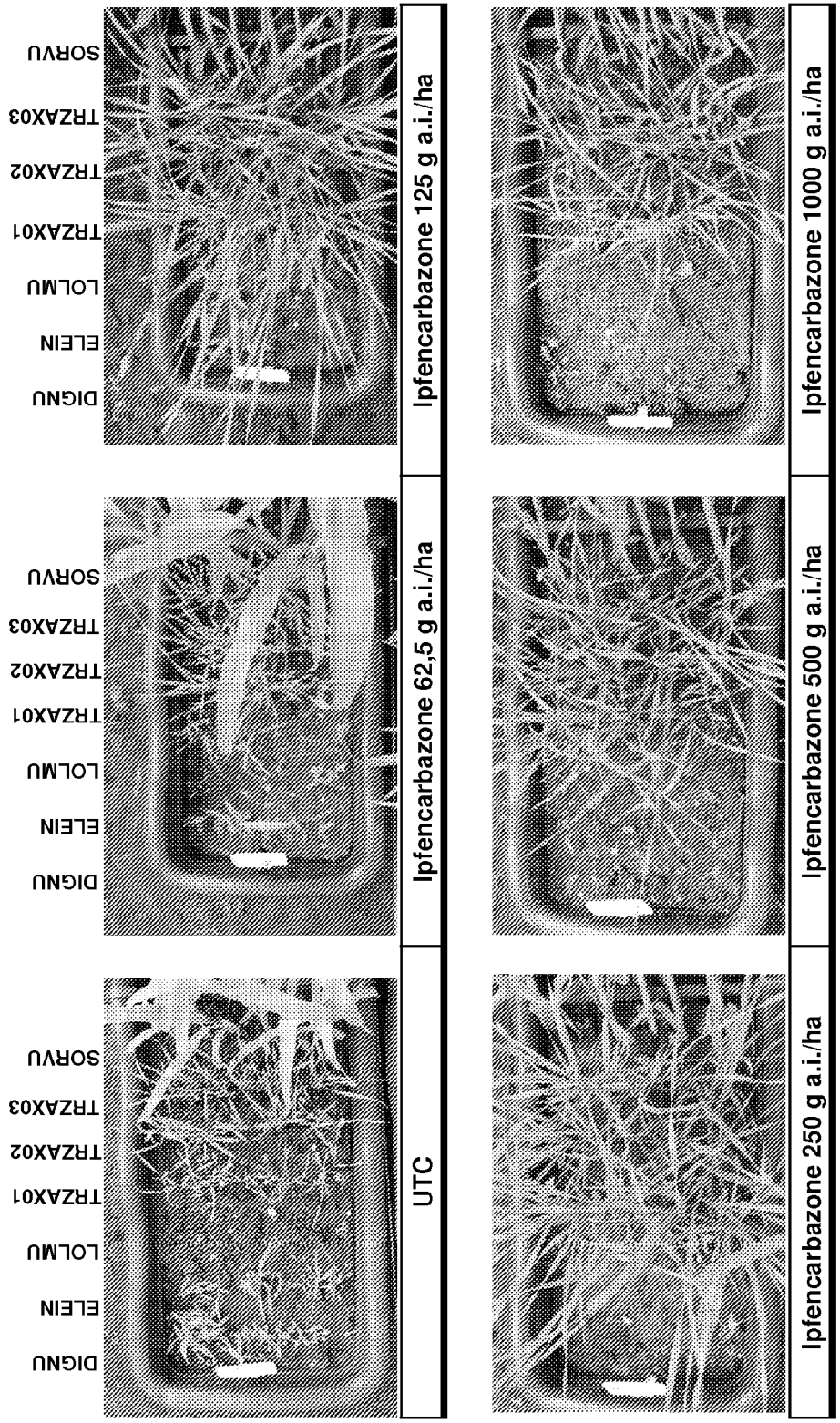
FIG. 7 shows photographs of test plants in an untreated control and with varying amounts of ipfencarbazone in grams of active ingredient per hectare; DIGNU: *Digitaria nuda*; ELEIN: *Eleusine indica*; LOLMU: *Lolium multiflorum*; TRZAX01: wheat cultivar Itaipú; TRZAX02: wheat cultivar Iguaçú; TRZAX03: wheat cultivar BRS327; SORVU: *Sorghum bicolor*.
Figure 8:
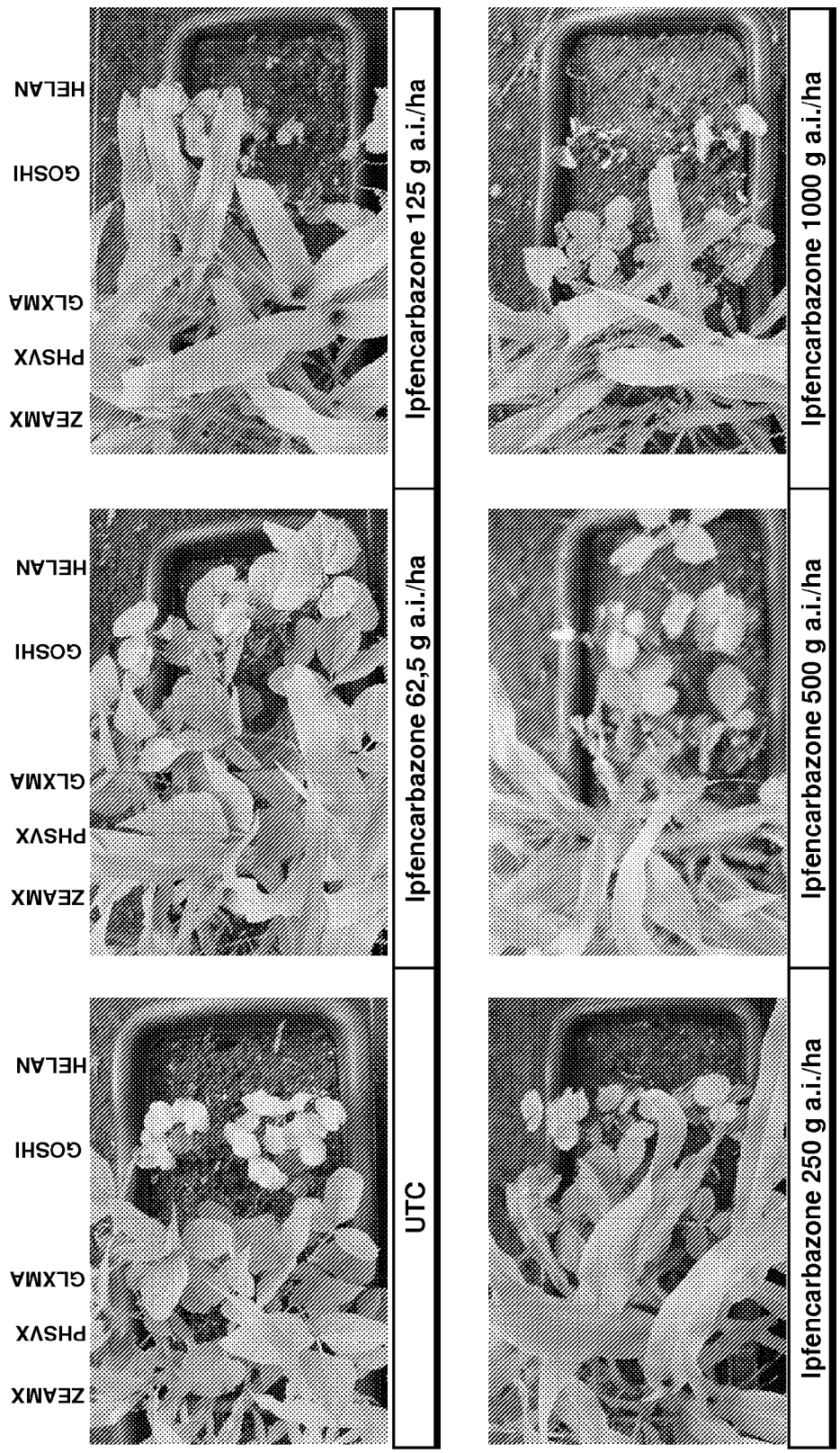
FIG. 8 shows photographs of trays containing multiple plant species that were either test plants in an untreated control or treated with varying amounts of ipfencarbazone in grams of active ingredient per hectare; ZEAMX: corn; PHSVX: dry bean; GLXMA: soybean; GOSHI: cotton; HELAN: sunflower.
Figure 9:
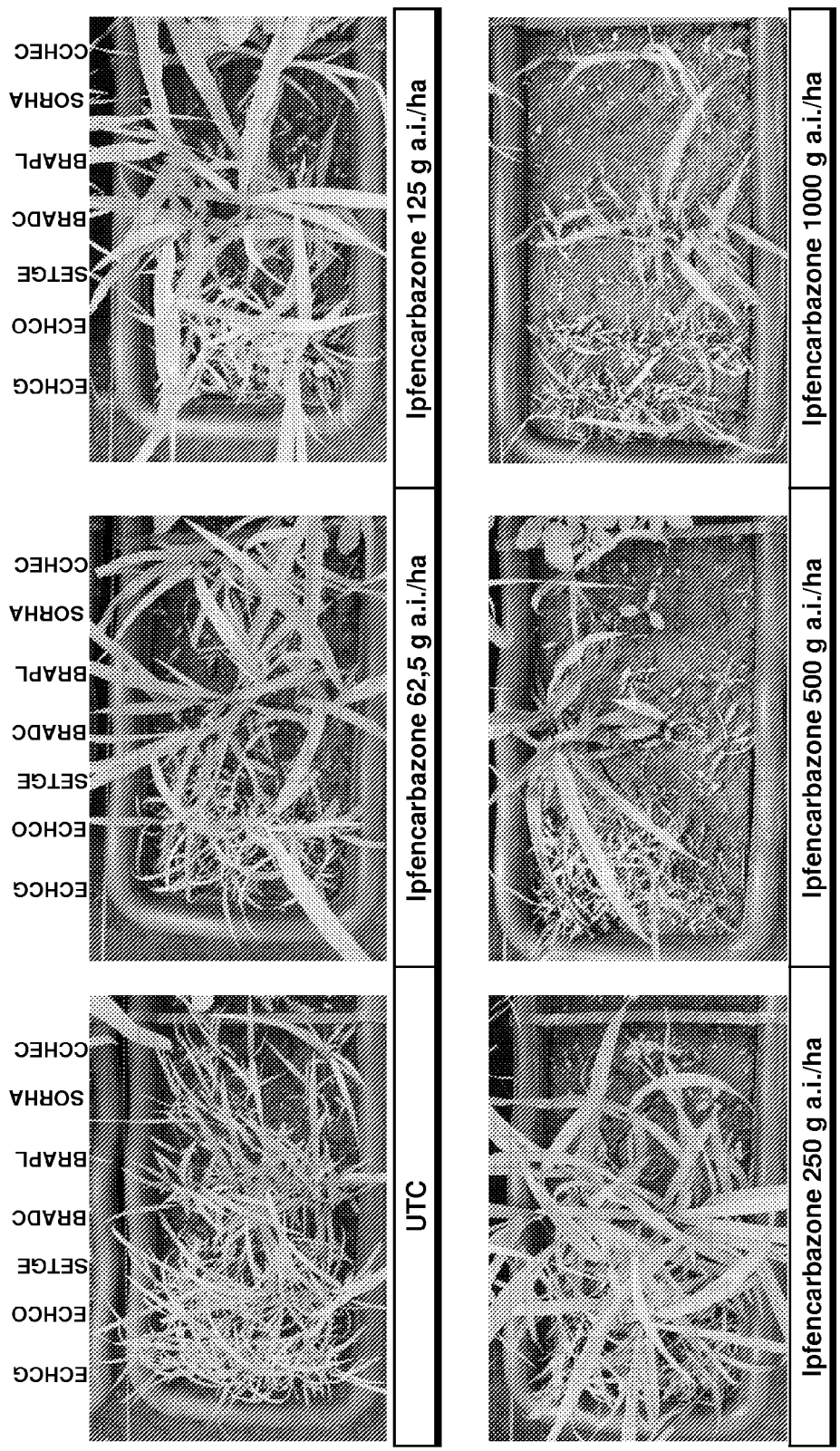
FIG. 9 shows photographs of trays containing multiple plant species that were either test plants in an untreated control or treated with varying amounts of ipfencarbazone in grams of active ingredient per hectare; ECHCG: *Echinochloa crus-galli*; ECGCO: *Echinochloa colona*; SETGE: *Setaria geniculata*; BRADC: *Brachiaria decumbens*; BRAPL: *Brachiaria plantaginea*; SORHA: *Sorghum halepense*; CCHEC: *Cenchrus echinatus*.
Figure 10:
FIG. 10 shows photographs of trays containing multiple plant species that were either test plants in an untreated control or treated with varying amounts of ipfencarbazone in grams of active ingredient per hectare; BIDPI: *Bidens pilosa*; RAPSR: *Raphanus sativus*; CASOB: *Cassia obtusi-* folia; EPHHL: *Euphorbia heterophylla*; IAQGR: *Ipomoea grandifolia*; AMAVI: *Amaranthus viridis*.

Methods: The indicated size pots (see Tables below) are filled with a specific soil, the soil properties being indicated below. The referenced crops and weeds are planted by hand in each pot. FIG. 3 shows three weeds plus four crops. FIG. 4 shows five crops. FIG. 5 shows seven grass weeds. FIG. 6 shows six broadleaf weeds. The experiments include six treatments each replicated three times on each crop/weed species. At a specific time after emergence each crop and weed species was treated with ipfencarbazone plus a non-ionic surfactant (NIS). In the present Example, the surfactant employed was ENERGIC™ (non-ionic surfactant). The application timing is indicated in each of the Tables (1 or 2 leaf stage) below. Ipfencarbazone plus surfactant was diluted in water and applied at a rate equivalent to about 250 L/ha. Ipfencarbazone was applied using a track sprayer. After treatment, the pots were randomized in a greenhouse. At each assessment (indicated by "days after treatment" or DAT) the height of each plant was measured. The data means are listed in the Tables below. The letters next to each mean indicate the level of statistical significance. Means with the same letters are not significantly different from each other.

Results: When applied post emergent ipfencarbazone demonstrated a significant, positive impact on plant growth. The affect was observed on all crop and weed species evaluated. The affect was observed at all use rates. There was a clear dose response and the response curve shifts to some degree according to species. Higher rates, 500 and 1000 g a.i./ha (grams active ingredient/hectare) demonstrated some herbicidal effect on specific crops and weeds. Surprisingly, positive growth effects in the treated plants is apparent in the following areas: plant height (measured), leaf area (visual observation), biomass, plant vigor (visual observation), plant color (visual observation)—significant greening effect compared to the untreated control.

A. Evaluation of ipfencarbazone biostimulant effect in wheat, *sorghum*, corn, soybean, dry bean and cotton—Early POST emergency application.

TABLE 1

| Trt No. | Type | Treatment Name | Form Conc | Form Unit | Form Type | Description | Rate | Rate Unit | Other Rate | Other Rate Unit |
|---|---|---|---|---|---|---|---|---|---|---|
| 1 | CHK | Untreated Check | | | | not treated | | | | |
| 2 | HERB | ARY-0572-001 | 248 | G/L | SC | ipfencarbazone | 62.5 | g ai/ha | 252 | ml-g/ha |
|   | ADJ | Energic | 226 | GA/L | CS | NIS | 113 | g ai/ha | 0.2 | % v/v |
| 3 | HERB | ARY-0572-001 | 248 | G/L | SC | ipfencarbazone | 125 | g ai/ha | 504 | ml-g/ha |
|   | ADJ | Energic | 226 | GA/L | CS | NIS | 113 | g ai/ha | 0.2 | % v/v |
| 4 | HERB | ARY-0572-001 | 248 | G/L | SC | ipfencarbazone | 250 | g ai/ha | 1010 | ml-g/ha |
|   | ADJ | Energic | 226 | GA/L | CS | NIS | 113 | g ai/ha | 0.2 | % v/v |
| 5 | HERB | ARY-0572-001 | 248 | G/L | SC | ipfencarbazone | 500 | g ai/ha | 2020 | ml-g/ha |
|   | ADJ | Energic | 226 | GA/L | CS | NIS | 113 | g ai/ha | 0.2 | % v/v |
| 6 | HERB | ARY-0572-001 | 248 | G/L | SC | ipfencarbazone | 1000 | g ai/ha | 4030 | ml-g/ha |
|   | ADJ | Energic | 226 | GA/L | CS | NIS | 113 | g ai/ha | 0.2 | % v/v |

Replications: 3, Untreated treatments: 1, Design: Randomized Complete Block (RCB), Treatment units: Treated 'Plot' experimental unit size, Dry Form. Unit: %, Treated 'Plot' experimental unit size Width: 1 meter, Treated 'Plot' experimental unit size Length: 1.4 meters, Application volume: 250 L/ha, Mix size: 0.15 liters, Product quantities used in the listed treatments and applications of trials are listed in Table 2:

TABLE 2

| Amount* | Unit | Treatment Name | Form Conc | Form Type |
|---|---|---|---|---|
| 4,688 | ml | ARY-0572-001 | 248 | SC |
| 1,500 | ml | Energic | 226 | CS |

*'Per area' calculations based on spray volume = 250 L/ha, mix size = 0.15 liters (mix size basis).

B. Evaluation of ipfencarbazone biostimulant effect in wheat, *sorghum*, corn, soybean, dry bean and cotton—Early post emergence application. In Table 3, ipfencarbazone biostimulant effect was evaluated when applied as early post treatment in wheat, *sorghum*, corn, soybean, dry bean and cotton. Ipfencarbazone demonstrate meaningful increase in growth rate (biomass, leaf area, plant height) when sprayed in wheat, *sorghum*, corn, soybean, dry bean and cotton.

TABLE 3

| | |
|---|---|
| Crop 1: TRZAX *Triticum aestivum* | Soft wheat |
| Variety: Itaipú | Planting Method: SEEDHA seeded by hand |
| | Emergence: 6 days after planting |
| Crop 2: TRZAX *Triticum aestivum* | Soft wheat |
| Variety: Iguaçú | Planting Method: SEEDHA seeded by hand |
| | Emergence: 6 days after planting |
| Crop 3: TRZAX *Triticum aestivum* | Soft wheat |
| Variety: BRS327 | Planting Method: SEEDHA seeded by hand |
| | Emergence: 6 days after planting |
| Crop 4: SORVU *Sorghum bicolor* | Grain sorghum |
| Variety: DKB590 | Planting Method: SEEDHA seeded by hand |
| | Emergence: 6 days after planting |
| Crop 5: ZEAMX *Zea mays* | Corn |
| Variety: AG7098PRO2 | Planting Method: SEEDHA seeded by hand |
| | Emergence: 6 days after planting |
| Crop 6: PHSVX *Phaseolus vulgaris* | Garden bean |
| Variety: PEROLA | Planting Method: SEEDHA seeded by hand |
| | Emergence: 6 days after planting |
| Crop 7: GLXMA *Glycine max* | Soybean |
| Variety: BMXPOTENCIA | Planting Method: SEEDHA seeded by hand |
| | Emergence: 6 days after planting |

TABLE 3-continued

| | |
|---|---|
| Crop 8: GOSHI *Gossypium hirsutum* | American upland cotton |
| Variety: 975WS | Planting Method: SEEDHA seeded by hand |
| | Emergence: 6 days after planting |
| Crop 9: BRADC *Brachiaria decumbens* | Surinam grass |
| Variety: BASILISK | Planting Method: SEEDHA seeded by hand |
| | Emergence: 6 days after planting |

TABLE 4

| Site and Design | |
|---|---|
| Treated Plot Width: 1 m | Site Type: GREENH greenhouse |
| Treated Plot Length: 1.4 m | Experimental Unit: 2 POT pot/container |
| Treated Plot Area: 1.4 m$^2$ | Tillage Type: CONTIL conventional-till |
| Treatments: 6 | Study Design: RACOBL Randomized Complete Block |
| Replications: 3 | (RCB) |

| Soil Description | |
|---|---|
| Description Name: JARDIPFENC | Texture: SCL sandy clay loam |
| % Sand: 73 % OM: 5 | Fert. Level: G good |
| % Silt: 2 pH: 5 | Soil Drainage: G good |
| % Clay: 26.8 CEC: 33 | |

| Additional Measured Elements | | |
|---|---|---|
| Element | Quantity | Unit |
| P | 2 | g dm$^3$ |
| K | 0.8 | mmol dm$^3$ |
| Ca | 8 | mmol dm$^3$ |
| Mg | 4 | mmol dm$^3$ |
| H + Al | 20 | mmol dm$^3$ |
| Al | 1 | mmol dm$^3$ |
| Cu | 0.2 | mg dm$^3$ |
| Fe | 4 | mg dm$^3$ |
| Zn | 0.3 | mg dm$^3$ |
| Mn | 2.2 | mg dm$^3$ |
| B | 0.35 | mg dm$^3$ |

| Application Description | |
|---|---|
| Appl. Start Time: | 14:50 |
| Appl. Stop Time: | 15:22 |
| Application Method: | SPRAY |
| Application Timing: | POSPOS |
| Application Placement: | FOLIAR |
| Air Temperature, Unit: | 32° C. |
| % Relative Humidity: | 40 |
| Wind Velocity, Unit: | 0.7 KPH |
| Dew Presence (Y/N): | N no |
| % Cloud Cover: | 0 |

C. Evaluation of ipfencarbazone biostimulant effect in wheat, *sorghum*, corn, soybean, dry bean and cotton—Early POST emergence application is shown below.

TABLE 5

| Pest Type | | | | | | | |
|---|---|---|---|---|---|---|---|
| Pest Code | | | | | | | |
| Pest Scientific Name | | | | | | | |
| Pest Name | | | | | | | |
| Crop Code | TRZAX | TRZAX | TRZAX | TRZAX | TRZAX | TRZAX | SORVU |
| BBCH Scale | BCER | BCER | BCER | BCER | BCER | BCER | BGRM |
| Crop Scientific Name | *Triticum aesti>* | *Triticum aesti>* | *Triticum aesti>* | *Triticum aesti>* | *Triticum aesti>* | *Triticum aesti>* | *Sorghum bicolor* |
| Crop Name | Soft wheat | Soft wheat | Soft wheat | Soft wheat | Soft wheat | Soft wheat | Grain *sorghum* |
| Crop Variety | Itaipú | Itaipú | Iguaçú | Iguaçú | BRS327 | BRS327 | DKB 590 |
| Part Rated | PLANT C | PLANT C | PLANT C | PLANT C | PLANT C | PLANT C | PLANT C |
| Rating Date | Oct. 24, 2014 | Nov. 6, 2014 | Oct. 24, 2014 | Nov. 6, 2014 | Oct. 24, 2014 | Nov. 6, 2014 | Oct. 24, 2014 |
| Rating Type | HEIGHT | HEIGHT | HEIGHT | HEIGHT | HEIGHT | HEIGHT | HEIGHT |
| Rating Unit | cm | cm | cm | cm | cm | cm | cm |
| Sample Size, Unit | 3 PLANT | 3 PLANT | 3 PLANT | 3 PLANT | 3 PLANT | 3 PLANT | 3 PLANT |
| Collection Basis, Unit | | | | | | | |
| Number of Subsamples | 3 | 3 | 3 | 3 | 3 | 3 | 3 |
| Crop Stage Majority | | | | | | | |
| Assessed By | | | | | | | |
| Rating Timing | | | | | | | |
| Days After First/Last Applic. | 15 | 28 | 15 | 28 | 15 | 28 | 15 |
| Trt-Eval Interval | 15 DA-A | 28 DA-A | 15 DA-A | 28 DA-A | 15 DA-A | 28 DA-A | 15 DA-A |
| Days After Emergence | 12 DE-1 | 25 DE-1 | 12 DE-1 | 25 DE-1 | 12 DE-1 | 25 DE-1 | 12 DE-1 |
| ARM Action Codes | APoC | APoC | APoC | APoC | APoC | APoC | APoC |
| Number of Decimal | 1 | 1 | 1 | 1 | 1 | 1 | 1 |

| Trt No. | Treatment Name | Description | Rate | Rate Unit | Other Rate | Other Rate Unit | 1 |
|---|---|---|---|---|---|---|---|
| 1 | Untreated Check | not treated | | | | | 14.1 c (100.0%) |
| 2 | ARY-0572-001 | Ipfencarbazone | 62.5 | g ai/ha | 252 | ml-g/ha | 23.8 abc (169.2%) |
|   | Energic | NIS | 113 | g ai/ha | 0.2 | % v/v | |
| 3 | ARY-0572-001 | Ipfencarbazone | 125 | g ai/ha | 504 | ml-g/ha | 25.5 ab (181.4%) |
|   | Energic | NIS | 113 | g ai/ha | 0.2 | % v/v | |
| 4 | ARY-0572-001 | Ipfencarbazone | 250 | g ai/ha | 1010 | ml-g/ha | 31.4 a (223.7%) |
|   | Energic | NIS | 113 | g ai/ha | 0.2 | % v/v | |
| 5 | ARY-0572-001 | Ipfencarbazone | 500 | g ai/ha | 2020 | ml-g/ha | 22.2 abc (157.7%) |
|   | Energic | NIS | 113 | g ai/ha | 0.2 | % v/v | |
| 6 | ARY-0572-001 | Ipfencarbazone | 1000 | g ai/ha | 4030 | ml-g/ha | 15.7 bc (111.5%) |
|   | Energic | NIS | 113 | g ai/ha | 0.2 | % v/v | |

| Trt No. | 2 | 3 | 4 | 5 | 6 | 7 |
|---|---|---|---|---|---|---|
| 1 | 24.0 a (100.0%) | 15.5 c (100.0%) | 22.6 c (100.0%) | 18.7 a (100.0%) | 22.3 a (100.0%) | 24.3 b (100.0%) |
| 2 | 37.1 a (154.6%) | 24.6 a (158.8%) | 29.2 bc (129.6%) | 27.2a (145.5%) | 33.0 a (147.8%) | 59.9 a (246.1%) |
| 3 | 32.3 a (134.7%) | 26.1 a (168.5%) | 30.1 be (133.5%) | 27.6 a (147.6%) | 35.0 a (156.7%) | 59.3 a (243.8%) |
| 4 | 47.8 a (199.1%) | 29.9 a (193.2%) | 43.3 a (192.1%) | 32.0 a (171.4%) | 45.6 a (204.0%) | 61.3 a (252.1%) |
| 5 | 24.0 a (100.0%) | 23.8 ab (153.4%) | 36.8 ab (163.1%) | 24.4 a (130.7%) | 31.6 a (141.3%) | 60.4 a (248.2%) |
| 6 | 18.4 a (76.9%) | 16.3 bc (105.4%) | 18.7 c (82.8%) | 17.3 a (92.9%) | 28.2 a (126.4%) | 22.7 b (93.2%) |
| LSD (P = .10) | 10.14 | 18.86 | 8.13 | 11.83 | 9.28 | 20.31 | 11.91 |
| Standard Deviation | 6.86 | 12.75 | 5.49 | 8.00 | 6.28 | 13.73 | 8.05 |
| CV | 31.02 | 41.64 | 24.18 | 26.56 | 25.59 | 42.09 | 16.78 |
| Bartlett's X2 | 8.098 | 4.827 | 6.08 | 1.968 | 10.254 | 16.569 | 7.041 |
| P(Bartlett's X2) | 0.151 | 0.437 | 0.299 | 0.854 | 0.068 | 0.005* | 0.218 |
| Skewness | 0.0663 | 0.0245 | 0.1083 | 0.2006 | −0.0442 | 0.0886 | −0.8046 |

TABLE 5-continued

|  | | | | | | | |
|---|---|---|---|---|---|---|---|
| Kurtosis | −1.5692 | −0.7714 | −1.1751 | −0.642 | 0.9485 | −0.9166 | −0.9142 |
| Replicate F | 0.340 | 0.267 | 1.057 | 0.659 | 1.808 | 1.655 | 0.765 |
| Replicate Prob(F) | 0.7200 | 0.7706 | 0.3832 | 0.5386 | 0.2137 | 0.2394 | 0.4909 |
| Treatment F | 2.653 | 2.124 | 3.208 | 3.829 | 2.409 | 0.953 | 16.689 |
| Treatment Prob(F) | 0.0888 | 0.1454 | 0.0551 | 0.0337 | 0.1109 | 0.4888 | 0.0001 |

Means followed by same letter do not significantly differ (P = .10, LSD)
t = Mean descriptions are reported in transformed data units, and are not de-transformed.
Mean comparisons performed only when AOV Treatment P (F) is significant at mean comparison OSL

TABLE 6

| Pest Type | | | | | | | |
|---|---|---|---|---|---|---|---|
| Pest Code | | | | | | | |
| Pest Scientific Name | | | | | | | |
| Pest Name | | | | | | | |
| Crop Code | SORVU | ZEAMX | ZEAMX | PHSVX | PHSVX | GLXMA | GLXMA |
| BBCH Scale | BGRM | BCOR | BCOR | BVBE | BVBE | BSOY | BSOY |
| Crop Scientific Name | Sorghum bicolor | Zea mays | Zea mays | Phaseolus vulg> | Phaseolus vulg> | Glycine max | Glycine max |
| Crop Name | Grain sorghum | Corn | Corn | Garden bean | Garden bean | Soybean | Soybean |
| Crop Variety | DKB 590 | AG7098PRO2 | AG7098PRO2 | PEROLA | PEROLA | BMXPOTENCIA | BMXPOTENCIA |
| Part Rated | PLANT C | PLANT C | PLANT C | PLANT C | PLANT C | PLANT C | PLANT C |
| Rating Date | Nov. 6, 2014 | Oct. 24, 2014 | Nov. 6, 2014 | Oct. 24, 2014 | Nov. 6, 2014 | Oct. 24, 2014 | Nov. 6, 2014 |
| Rating Type | HEIGHT | HEIGHT | HEIGHT | HEIGHT | HEIGHT | HEIGHT | HEIGHT |
| Rating Unit | cm | cm | cm | cm | cm | cm | cm |
| Sample Size, Unit | 3 PLANT | 3 PLANT | 3 PLANT | 3 PLANT | 3 PLANT | 3 PLANT | 3 PLANT |
| Collection Basis, Unit | | | | | | | |
| Number of Subsamples | 3 | 3 | 3 | 3 | 3 | 3 | 3 |
| Crop Stage Majority Assessed By Rating Timing | | | | | | | |
| Days After First/Last Applic. | 28 | 15 | 28 | 15 | 28 | 15 | 28 |
| Trt-Eval Interval | 28 DA-A | 15 DA-A | 28 DA-A | 15 DA-A | 28 DA-A | 15 DA-A | 28 DA-A |
| Days After Emergence | 25 DE-1 | 12 DE-1 | 25 DE-1 | 12 DE-1 | 25 DE-1 | 12 DE-1 | 25 DE-1 |
| ARM Action Codes | APoC | APoC | APoC | APoC | AS APoC | APoC | APoC |
| Number of Decimals | 1 | 1 | 1 | 1 | 1 | 1 | 1 |

| Trt No. | Treatment Name | Description | Rate | Rate Unit | Other Rate | Other Rate Unit | 8 |
|---|---|---|---|---|---|---|---|
| 1 | Untreated Check | not treated | | | | | 28.7b (100.0%) |
| 2 | ARY-0572-001 | Ipfencarbazone | 62.5 | g ai/ha | 252 | ml-g/ha | 85.0 a |
|  | Energic | NIS | 113 | g ai/ha | 0.2 | % v/v | (296.5%) |
| 3 | ARY-0572-001 | Ipfencarbazone | 125 | g ai/ha | 504 | ml-g/ha | 79.4 a |
|  | Energic | NIS | 113 | g ai/ha | 0.2 | % v/v | (277.1%) |
| 4 | ARY-0572-001 | Ipfencarbazone | 250 | g ai/ha | 1010 | ml-g/ha | 101.8 a |
|  | Energic | NIS | 113 | g ai/ha | 0.2 | % v/v | (355.0%) |
| 5 | ARY-0572-001 | Ipfencarbazone | 500 | g ai/ha | 2020 | ml-g/ha | 76.4 a |
|  | Energic | NIS | 113 | g ai/ha | 0.2 | % v/v | (266.7%) |
| 6 | ARY-0572-001 | Ipfencarbazone | 1000 | g ai/ha | 4030 | ml-g/ha | 35.4 b |
|  | Energic | NIS | 113 | g ai/ha | 0.2 | % v/v | (123.6%) |

| Trt No. | 9 | 10 | 11 | 12 | 13 | 14 |
|---|---|---|---|---|---|---|
| 1 | 38.2b (100.0%) | 50.9b (100.0%) | 9.9ab (100.0%) | 13.0a (100.0%) | 13.2ab (100.0%) | 20.9abc (100.0%) |
| 2 | 56.1 a (146.7%) | 89.4 a (175.8%) | 10.4 a (105.6%) | 19.8 a (152.2%) | 15.0 a (113.4%) | 30.6a (146.3%) |
| 3 | 59.8 a (156.4%) | 85.9 a (168.8%) | 7.5 ab (75.8%) | 12.0 a (91.8%) | 11.2 abc (84.9%) | 23.8 ab (113.3%) |
| 4 | 59.4 a (155.4%) | 106.0 a (208.3%) | 0.6 c (5.6%) | 0.3 a (2.5%) | 9.5 bcd (71.8%) | 18.3 bc (87.8%) |
| 5 | 61.9 a (161.9%) | 104.8 a (205.9%) | 0.7 c (6.7%) | 20.2 a (155.1%) | 6.0 d (45.4%) | 13.2 c (63.3%) |

TABLE 6-continued

| | | | | | | | |
|---|---|---|---|---|---|---|---|
| 6 | 37.6 b (98.3%) | 60.0 b (117.9%) | 5.8 b (59.0%) | 6.7 a (51.7%) | 8.7 cd (65.5%) | 14.9 bc (71.3%) | |
| | | LSD (P = .10) | 35.22 | 8.79 | 22.95 | 4.50 | 2.49t | 3.94 | 9.79 |
| | | Standard Deviation | 23.81 | 5.94 | 15.51 | 3.04 | 1.69t | 2.66 | 6.62 |
| | | CV | 35.12 | 11.4 | 18.73 | 52.26 | 50.89 | 25.13 | 32.65 |
| | | Bartlett's X2 | 13.787 | 5.509 | 15.782 | 14.139 | 23.093 | 12.712 | 8.416 |
| | | P(Bartlett's X2) | 0.017* | 0.357 | 0.007* | 0.015* | 0.001* | 0.026* | 0.135 |
| | | Skewness | −0.4047 | −0.7333 | −0.5321 | −0.0914 | 0.4892 | −0.7512 | −0.8524 |
| | | Kurtosis | −1.2664 | −0.7675 | −1.4491 | −1.7617 | 0.7875 | 0.4351 | 1.4394 |
| | | Replicate F | 0.146 | 0.768 | 0.505 | 0.474 | 0.418 | 0.768 | 0.134 |
| | | Replicate Prob(F) | 0.8658 | 0.4897 | 0.6181 | 0.6359 | 0.6694 | 0.4895 | 0.8765 |
| | | Treatment F | 4.487 | 10.665 | 6.514 | 6.174 | 1.964 | 4.458 | 2.750 |
| | | Treatment Prob(F) | 0.0210 | 0.0009 | 0.0061 | 0.0073 | 0.1702 | 0.0214 | 0.0814 |

TABLE 7

| | | | | |
|---|---|---|---|---|
| Pest Type | | | | |
| Pest Code | | | | |
| Pest Scientific Name | | | | |
| Pest Name | | | | |
| Crop Code | GOSHI | GOSHI | BRADC | BRADC |
| BBCH Scale | BCOT | BCOT | BGRM | BGRM |
| Crop Scientific Name | *Gossypium hirs>* | *Gossypium hirs>* | *Brachiaria dec>* | *Brachiaria dec>* |
| Crop Name | American uplan> | American uplan> | Surinam grass | Surinam grass |
| Crop Variety | 975WS | 975WS | BASILISK | BASILISK |
| Part Rated | PLANT C | PLANT C | PLANT C | PLANT C |
| Rating Date | Oct. 24, 2014 | Nov. 6, 2014 | Oct. 24, 2014 | Nov. 6, 2014 |
| Rating Type | HEIGHT | HEIGHT | HEIGHT | HEIGHT |
| Rating Unit | cm | cm | cm | cm |
| Sample Size, Unit | 3 PLANT | 3 PLANT | 3 PLANT | 3 PLANT |
| Collection Basis, Unit | | | | |
| Number of Subsamples | 3 | 3 | 3 | 3 |
| Crop Stage Majority Assessed By | | | | |
| Rating Timing | | | | |
| Days After First/Last Applic. | 15 | 28 | 15 | 28 |
| Trt-Eval Interval | 15 DA-A | 28 DA-A | 15 DA-A | 28 DA-A |
| Days After Emergence | 12 DE-1 | 25 DE-1 | 12 DE-1 | 25 DE-1 |
| ARM Action Codes | APoC | APoC | APoC | APoC |
| Number of Decimals | 1 | 1 | 1 | 1 |

| Trt No. | Treatment Name | Description | Rate | Rate Unit | Other Rate |
|---|---|---|---|---|---|
| 1 | Untreated Check | not treated | | | |
| 2 | ARY-0572-001 | Ipfencarbazone | 62.5 | g ai/ha | 252 |
| | Energic | NIS | 113 | g ai/ha | 0.2 |
| 3 | ARY-0572-001 | Ipfencarbazone | 125 | g ai/ha | 504 |
| | Energic | NIS | 113 | g ai/ha | 0.2 |
| 4 | ARY-0572-001 | Ipfencarbazone | 250 | g ai/ha | 1010 |
| | Energic | NIS | 113 | g ai/ha | 0.2 |
| 5 | ARY-0572-001 | Ipfencarbazone | 500 | g ai/ha | 2020 |
| | Energic | NIS | 113 | g ai/ha | 0.2 |
| 6 | ARY-0572-001 | Ipfencarbazone | 1000 | g ai/ha | 4030 |
| | Energic | NIS | 113 | g ai/ha | 0.2 |

| Trt No. | Other Rate Unit | 15 | 16 | 17 | 18 |
|---|---|---|---|---|---|
| 1 | | 11.7 b (100.0%) | 16.1 bc (100.0%) | 20.2 bc (100.0%) | 33.8 de (100.0%) |
| 2 | ml-g/ha % v/v | 16.1 a (137.6%) | 24.9 a (154.5%) | 33.8 a (167.8%) | 55.4 bc (164.1%) |

TABLE 7-continued

| | | | | | |
|---|---|---|---|---|---|
| 3 | ml-g/ha | 11.9 b | 17.7 ab | 28.1 ab | 49.6 cd |
| | % v/v | (101.9%) | (109.7%) | (139.1%) | (146.7%) |
| 4 | mi-g/ha | 9.5 bc | 15.8 bc | 28.5 ab | 78.9 a |
| | % v/v | (81.4%) | (97.9%) | (141.3%) | (233.6%) |
| 5 | mi-g/ha | 7.7 c | 13.2 bc | 18.8 bc | 71.1 ab |
| | % v/v | (66.2%) | (82.1%) | (93.1%) | (210.5%) |
| 6 | mi-g/ha | 6.9 c | 8.9 c | 10.9 c | 25.0 e |
| | % v/v | (59.5%) | (55.2%) | (54.0%) | (74.0%) |

| | | | | |
|---|---|---|---|---|
| LSD (P = .10) | 3.20 | 7.45 | 12.15 | 19.79 |
| Standard Deviation | 2.17 | 5.04 | 8.21 | 13.38 |
| CV | 20.37 | 31.29 | 35.14 | 25.58 |
| Bartlett's X2 | 5.52 | 6.709 | 4.04 | 8.331 |
| P(Bartlett's X2) | 0.356 | 0.243 | 0.544 | 0.139 |
| Skewness | 0.6265 | −0.0409 | 0.3061 | 0.0601 |
| Kurtosis | 0.2968 | −0.6152 | 0.0991 | −0.4929 |
| Replicate F | 2.032 | 0.799 | 1.138 | 1.662 |
| Replicate Prob(F) | 0.1818 | 0.4765 | 0.3587 | 0.2381 |
| Treatment F | 7.088 | 3.314 | 3.068 | 7.265 |
| Treatment Prob(F) | 0.0045 | 0.0505 | 0.0619 | 0.0041 |

D. Evaluation of ipfencarbazone biostimulant effect in wheat, *sorghum*, corn, soybean, dry bean and cotton—Early POST emergency application is shown below.

TABLE 8

Crop Code

TRZAX, BCER, *Triticum aestivum*, = US
SORVU, BGRM, *Sorghum bicolor*, = US
ZEAMX, BCOR, *Zea mays*, = US
PHSVX, BVBE, *Phaseolus vulgaris*, = US
GLXMA, BSOY, *Glycine max*, = US
GOSHI, BCOT, *Gossypium hirsutum*, = US
BRADC, BGRM, *Brachiaria decumbens*, = US
Part Rated PLANT = plant
C = Crop is Part Rated TABLE 8-continued Rating Type HEIGHT = height
Rating Unit cm = centimeter
PLANT = plant/plant biomass/shrub
ARM Action Codes APoC = Automatic percent control (Control forced to 100% on AOV Means Table)
AS = Automatic square root transformation of X + 0.5

E. Evaluation of ipfencarbazone biostimulant effect in wheat, *sorghum*, corn, soybean, dry bean and cotton—Early POST emergency application is shown below.

TABLE 9

| | | | | | | | |
|---|---|---|---|---|---|---|---|
| Pest Type | | | | | | | |
| Pest Code | | | | | | | |
| Pest Scientific Name | | | | | | | |
| Pest Name | | | | | | | |
| Crop Code | TRZAX | TRZAX | TRZAX | TRZAX | TRZAX | TRZAX | SORVU |
| BBCH Scale | BCER | BCER | BCER | BCER | BCER | BCER | BGRW |
| Crop Scientific Name | *Triticum aesti>* | *Triticum aesti>* | *Triticum aesti>* | *Triticum aesti>* | *Triticum aesti>* | *Triticum aesti>* | *Sorghum bicolor* |
| Crop Name | Soft wheat | Soft wheat | Soft wheat | Soft wheat | Soft wheat | Soft wheat | Grain *sorghum* |
| Crop Variety | Itaipú | Itaipú | Iguaçú | Iguaçú | BRS327 | BRS327 | DKB 590 |
| Part Rated | PLANT C | PLANT C | PLANT C | PLANT C | PLANT C | PLANT C | PLANT C |
| Rating Date | Oct. 24, 2014 | Nov. 6, 2014 | Oct. 24, 2014 | Nov. 6, 2014 | Oct. 24, 2014 | Nov. 6, 2014 | Oct. 24, 2014 |
| Rating Type | HEIGHT | HEIGHT | HEIGHT | HEIGHT | HEIGHT | HEIGHT | HEIGHT |
| Rating Unit | cm | cm | cm | cm | cm | cm | cm |
| Sample Size, Unit | 3 PLANT | 3 PLANT | 3 PLANT | 3 PLANT | 3 PLANT | 3 PLANT | 3 PLANT |
| Collection Basis, Unit | | | | | | | |
| Number of Subsamples | 3 | 3 | 3 | 3 | 3 | 3 | 3 |
| Crop Stage Majority | | | | | | | |
| Assessed By | | | | | | | |
| Rating Timing | | | | | | | |
| Days After First/Last Applic. | 15 | 28 | 15 | 28 | 15 | 28 | 15 |
| Trt-Eval Interval | 15 DA-A | 28 DA-A | 15 DA-A | 28 DA-A | 15 DA-A | 28 DA-A | 15 DA-A |
| Days After Emergence | 12 DE-1 | 25 DE-1 | 12 DE-1 | 25 DE-1 | 12 DE-1 | 25 DE-1 | 12 DE-1 |

TABLE 9-continued

| Trt No. | Treatment Name | Description | Rate | Rate Unit | Other Rate | Other Rate Unit | Plot | 1 | 2 | 3 | 4 | 5 | 6 | 7 |
|---|---|---|---|---|---|---|---|---|---|---|---|---|---|---|
| ARM Action Codes | | | | | | | | APoC | APoC | APoC | APoC | APoC | APoC | APoC |
| Number of Decimals | | | | | | | | 1 | 1 | 1 | 1 | 1 | 1 | 1 |
| 1 | Untreated Check | not treated | | | | | 101 | 11.2 | 17.3 | 13.2 | 19.3 | 15.7 | 21.3 | 26.3 |
| | | | | | | | 204 | 14.7 | 23.0 | 14.7 | 21.7 | 19.7 | 20.0 | 24.3 |
| | | | | | | | 303 | 16.3 | 31.7 | 18.7 | 26.7 | 20.7 | 25.7 | 22.3 |
| | | | | | | | Mean = | 14.1 | 24.0 | 15.5 | 22.6 | 18.7 | 22.3 | 24.3 |
| 2 | ARY-0572-001 Energic | Ipfen-carbazone | 62.5 | g ai/ha | 252 | ml-g/ha | 102 | 16.0 | 26.0 | 20.2 | 24.0 | 25.0 | 27.7 | 55.3 |
| | | NIS | 113 | g ai/ha | 0.2 | % v/v | 205 | 33.0 | 54.0 | 28.0 | 36.3 | 30.8 | 43.3 | 68.0 |
| | | | | | | | 302 | 22.3 | 31.3 | 25.7 | 27.3 | 25.7 | 28.0 | 56.3 |
| | | | | | | | Mean = | 23.8 | 37.1 | 24.6 | 29.2 | 27.2 | 33.0 | 59.9 |
| 3 | ARY-0572-001 Energic | Ipfen-carbazone | 125 | g ai/ha | 504 | ml-g/ha | 103 | 33.3 | 45.0 | 35.7 | 39.7 | 39.0 | 49.0 | 68.7 |
| | | NIS | 113 | g ai/ha | 0.2 | % v/v | 206 | 19.8 | 23.3 | 16.3 | 20.7 | 15.7 | 24.7 | 55.0 |
| | | | | | | | 305 | 23.3 | 28.7 | 26.3 | 30.0 | 28.0 | 31.3 | 54.3 |
| | | | | | | | Mean = | 25.5 | 32.3 | 26.1 | 30.1 | 27.6 | 35.0 | 59.3 |
| 4 | ARY-0572-001 Energic | Ipfen-carbazone | 250 | g ai/ha | 1010 | mi-g/ha | 104 | 30.7 | 45.0 | 28.3 | 39.7 | 31.0 | 45.7 | 58.0 |
| | | NIS | 113 | g ai/ha | 0.2 | % v/v | 201 | 31.3 | 46.7 | 30.7 | 50.3 | 32.3 | 46.0 | 65.0 |
| | | | | | | | 306 | 32.3 | 51.7 | 30.8 | 40.0 | 32.7 | 45.0 | 61.0 |
| | | | | | | | Mean = | 31.4 | 47.8 | 29.9 | 43.3 | 32.0 | 45.6 | 61.3 |
| 5 | ARY-0572-001 Energic | Ipfen-carbazone | 500 | g ai/ha | 2020 | mi-g/ha | 105 | 29.7 | 4.0 | 30.3 | 47.0 | 30.7 | 38.7 | 56.0 |
| | | NIS | 113 | g ai/ha | 0.2 | % v/v | 202 | 11.5 | 26.0 | 18.7 | 27.7 | 14.2 | 13.3 | 66.3 |
| | | | | | | | 301 | 25.3 | 42.0 | 22.3 | 35.7 | 28.3 | 42.7 | 58.8 |
| | | | | | | | Mean = | 22.2 | 24.0 | 23.8 | 36.8 | 24.4 | 31.6 | 60.4 |
| 6 | ARY-0572-001 Energic | Ipfen-carbazone | 1000 | g ai/ha | 4030 | mi-g/ha | 106 | 22.0 | 28.7 | 22.3 | 29.3 | 23.3 | 59.7 | 39.3 |
| | | NIS | 113 | g ai/ha | 0.2 | % v/v | 203 | 13.0 | 14.3 | 14.0 | 14.0 | 11.7 | 9.0 | 12.0 |
| | | | | | | | 304 | 12.0 | 12.3 | 12.7 | 12.7 | 17.0 | 16.0 | 16.7 |
| | | | | | | | Mean = | 15.7 | 18.4 | 16.3 | 18.7 | 17.3 | 28.2 | 22.7 |

TABLE 10

| | | | | | | |
|---|---|---|---|---|---|---|
| Pest Type | | | | | | |
| Pest Code | | | | | | |
| Pest Scientific Name | | | | | | |
| Pest Name | | | | | | |
| Crop Code | SORVU | ZEAMX | ZEAMX | PHSVX | PHSVX | GLXMA |
| BBCH Scale | BGRM | BCOR | BCOR | BVBE | BVBE | BSOY |
| Crop Scientific Name | *Sorghum bicolor* | *Zea mays* | *Zea mays* | *Phaseolus vulg>* | *Phaseolus vulg>* | *Glycine max* |
| Crop Name | Grain sorghum | Corn | Corn | Garden bean | Garden bean | Soybean |
| Crop Variety | DKB 590 | AG7098PRO2 | AG7098PRO2 | PEROLA | PEROLA | BMXPOTENCIA |
| Part Rated | PLANT C | PLANT C | PLANT C | PLANT C | PLANT C | PLANT C |
| Rating Date | Nov. 6, 2014 | Oct. 24, 2014 | Nov. 6, 2014 | Oct. 24, 2014 | Nov. 6, 2014 | Oct. 24, 2014 |
| Rating Type | HEIGHT | HEIGHT | HEIGHT | HEIGHT | HEIGHT | HEIGHT |
| Rating Unit | cm | cm | cm | cm | cm | cm |
| Sample Size, Unit | 3 PLANT | 3 PLANT | 3 PLANT | 3 PLANT | 3 PLANT | 3 PLANT |
| Collection Basis, Unit | | | | | | |
| Number of Subsamples | 3 | 3 | 3 | 3 | 3 | 3 |
| Crop Stage Majority | | | | | | |
| Assessed By | | | | | | |
| Rating Timing | | | | | | |
| Days After First/Last Applic. | 28 | 15 | 28 | 15 | 28 | 15 |
| Trt-Eval Interval | 28 DA-A | 15 DA-A | 28 DA-A | 15 DA-A | 28 DA-A | 15 DA-A |
| Days After Emergence | 25 DE-1 | 12 DE-1 | 25 DE-1 | 12 DE-1 | 25 DE-1 | 12 DE-1 |
| ARM Action Codes | APoC | ApoC | ApoC | ApoC | AS ApoC | ApoC |
| Number of Decimals | 1 | 1 | 1 | 1 | 1 | 1 |

TABLE 10-continued

| Trt No. | Treatment Name | Description | Rate | Rate Unit | Other Rate | Other Rate Unit | Plot | 8 | 9 | 10 | 11 | 12 | 13 |
|---|---|---|---|---|---|---|---|---|---|---|---|---|---|
| 1 | Untreated Check | not treated | | | | | 101 | 29.7 | 34.3 | 48.3 | 10.3 | 10.7 | 13.0 |
| | | | | | | | 204 | 26.0 | 39.0 | 52.0 | 10.3 | 14.3 | 14.0 |
| | | | | | | | 303 | 30.3 | 41.3 | 52.3 50.9 | 9.0 | 14.7 | 12.7 |
| | | | | | | | Mean = | 28.7 | 38.2 | | 9.9 | 13.0t | 13.2 |
| 2 | ARY-0572-001 Energic | Ipfen-carbazone | 62.5 | g ai/ha | 252 | ml-g/ha | 102 | 73.0 | 52.3 | 71.3 | 11.7 | 24.0 | 15.3 |
| | | NIS | 113 | g ai/ha | 0.2 | % v/v | 205 | 110.7 | 64.8 | 106.7 | 8.0 | 17.3 | 14.8 |
| | | | | | | | 302 | 71.3 | 51.0 | 90.3 | 11.7 | 19.7 | 14.8 |
| | | | | | | | Mean = | 85.0 | 56.1 | 89.4 | 10.4 | 19.8t | 15.0 |
| 3 | ARY-0572-001 Energic | Ipfen-carbazone | 125 | g ai/ha | 504 | ml-g/ha | 103 | 102.7 | 62.7 | 103.0 | 0.0 | 4.3 | 6.2 |
| | | NIS | 113 | g ai/ha | 0.2 | % v/v | 206 | 71.3 | 59.0 | 82.0 | 10.7 | 16.0 | 13.5 |
| | | | | | | | 305 | 64.3 | 57.7 | 72.7 | 11.8 | 20.3 | 14.0 |
| | | | | | | | Mean = | 79.4 | 59.8 | 85.9 | 7.5 | 12.0t | 11.2 |
| 4 | ARY-0572-001 Energic | Ipfen-carbazone | 250 | g ai/ha | 1010 | mi-g/ha | 104 | 101.3 | 56.5 | 108.3 | 0.0 | 0.0 | 8.3 |
| | | NIS | 113 | g ai/ha | 0.2 | % v/v | 201 | 104.0 | 61.0 | 104.0 | 1.7 | 2.0 | 10.8 |
| | | | | | | | 306 | 100.0 | 60.7 | 105.7 | 0.0 | 0.0 | 9.3 |
| | | | | | | | Mean = | 101.8 | 59.4 | 106.0 | 0.6 | 0.3t | 9.5 |
| 5 | ARY-0572-001 Energic | Ipfen-carbazone | 500 | g ai/ha | 2020 | mi-g/ha | 105 | 44.7 | 58.7 | 101.7 | 2.0 | 73.0 | 8.0 |
| | | NIS | 113 | g ai/ha | 0.2 | % v/v | 202 | 89.7 | 67.0 | 107.7 | 0.0 | 0.0 | 1.3 |
| | | | | | | | 301 | 95.0 | 60.0 | 105.0 | 0.0 | 25.0 | 8.7 |
| | | | | | | | Mean = | 76.4 | 61.9 | 104.8 | 0.7 | 20.2t | 6.0 |
| 6 | ARY-0572-001 Energic | Ipfen-carbazone | 1000 | g ai/ha | 4030 | mi-g/ha | 106 | 75.3 | 48.7 | 91.7 | 5.0 | 6.3 | 6.7 |
| | | NIS | 113 | g ai/ha | 0.2 | % v/v | 203 | 9.3 | 34.7 | 44.0 | 6.7 | 7.3 | 10.0 |
| | | | | | | | 304 | 21.7 | 29.3 | 44.3 | 5.8 | 6.7 | 9.3 |
| | | | | | | | Mean = | 35.4 | 37.6 | 60.0 | 5.8 | 6.7t | 8.7 |

TABLE 11

| | | | | | |
|---|---|---|---|---|---|
| Pest Type | | | | | |
| Pest Code | | | | | |
| Pest Scientific Name | | | | | |
| Pest Name | | | | | |
| Crop Code | GLXMA | GOSHI | GOSHI | BRADC | BRADC |
| BBCH Scale | BSOY | BCOT | BCOT | BGRM | BGRM |
| Crop Scientific Name | *Glycine max* | *Gossypium hirs>* | *Gossypium hirs>* | *Brachiaria dec>* | *Brachiaria dec>* |
| Crop Name | Soybean | American uplan> | American uplan> | Surinam grass | Surinam grass |
| Crop Variety | BMXPOTENCIA | 975WS | 975WS | BASILISK | BASILISK |
| Part Rated | PLANT C | PLANT C | PLANT C | PLANT C | PLANT C |
| Rating Date | Nov. 6, 2014 | Oct. 24, 2014 | Nov. 6, 2014 | Oct. 24, 2014 | Nov. 6, 2014 |
| Rating Type | HEIGHT | HEIGHT | HEIGHT | HEIGHT | HEIGHT |
| Rating Unit | cm | cm | cm | cm | cm |
| Sample Size, Unit | 3 PLANT | 3 PLANT | 3 PLANT | 3 PLANT | 3 PLANT |
| Collection Basis, Unit | | | | | |
| Number of Subsamples | 3 | 3 | 3 | 3 | 3 |
| Crop Stage Majority Assessed By Rating Timing | | | | | |
| Days After First/Last Applic. | 28 | 15 | 28 | 15 | 28 |
| Trt-Eval Interval | 28 DA-A | 15 DA-A | 28 DA-A | 15 DA-A | 28 DA-A |
| Days After Emergence | 25 DE-1 | 12 DE-1 | 25 DE-1 | 12 DE-1 | 25 DE-1 |
| ARM Action Codes | APoC | APoC | APoC | APoC | APoC |
| Number of Decimals | 1 | 1 | 1 | 1 | 1 |

TABLE 11-continued

| Trt No. | Treatment Name | Description | Rate | Rate Unit | Other Rate | Other Rate Unit | Plot | 8 | 9 | 10 | 11 | 12 |
|---|---|---|---|---|---|---|---|---|---|---|---|---|
| 1 | Untreated Check | not treated | | | | | 101 | 19.0 | 11.0 | 16.3 | 17.7 | 32.0 |
| | | | | | | | 204 | 23.3 | 8.7 | 12.7 | 25.7 | 38.7 |
| | | | | | | | 303 | 20.3 | 15.3 | 19.3 | 17.2 | 30.7 |
| | | | | | | | Mean = | 20.9 | 11.7 | 16.1 | 20.2 | 33.8 |
| 2 | ARY-0572-001 Energic | Ipfencarbazone NIS | 62.5 113 | g ai/ha g ai/ha | 252 0.2 | ml-g/ha % v/v | 102 | 32.7 | 19.2 | 26.0 | 26.8 | 48.3 |
| | | | | | | | 205 | 29.3 | 13.7 | 27.7 | 44.7 | 76.0 |
| | | | | | | | 302 | 29.7 | 15.3 | 21.0 | 30.0 | 42.0 |
| | | | | | | | Mean = | 30.6 | 16.1 | 24.9 | 33.8 | 55.4 |
| 3 | ARY-0572-001 Energic | Ipfencarbazone NIS | 125 113 | g ai/ha g ai/ha | 504 0.2 | ml-g/ha % v/v | 103 | 20.7 | 9.7 | 19.0 | 27.8 | 53.0 |
| | | | | | | | 206 | 22.7 | 12.0 | 17.3 | 23.7 | 44.7 |
| | | | | | | | 305 | 28.0 | 14.0 | 16.7 | 32.7 | 51.0 |
| | | | | | | | Mean = | 23.8 | 11.9 | 17.7 | 28.1 | 49.6 |
| 4 | ARY-0572-001 Energic | Ipfencarbazone NIS | 250 113 | g ai/ha g ai/ha | 1010 0.2 | mi-g/ha % v/v | 104 | 20.3 | 9.3 | 23.7 | 14.0 | 89.7 |
| | | | | | | | 201 | 21.7 | 9.2 | 18.3 | 42.0 | 91.7 |
| | | | | | | | 306 | 13.0 | 10.0 | 5.3 | 29.5 | 55.3 |
| | | | | | | | Mean = | 18.3 | 9.5 | 15.8 | 28.5 | 78.9 |
| 5 | ARY-0572-001 Energic | Ipfencarbazone NIS | 500 113 | g ai/ha g ai/ha | 2020 0.2 | mi-g/ha % v/v | 105 | 24.7 | 9.2 | 18.0 | 21.3 | 67.3 |
| | | | | | | | 202 | 0.0 | 6.3 | 8.7 | 21.3 | 77.0 |
| | | | | | | | 301 | 15.0 | 7.7 | 13.0 | 13.7 | 69.0 |
| | | | | | | | Mean = | 13.2 | 7.7 | 13.2 | 18.8 | 71.1 |
| 6 | ARY-0572-001 Energic | Ipfencarbazone NIS | 1000 113 | g ai/ha g ai/ha | 4030 0.2 | mi-g/ha % v/v | 106 | 9.0 | 4.3 | 6.0 | 20.0 | 47.3 |
| | | | | | | | 203 | 18.0 | 7.0 | 8.0 | 7.7 | 10.7 |
| | | | | | | | 304 | 17.7 | 9.5 | 12.7 | 5.0 | 17.0 |
| | | | | | | | Mean = | 14.9 | 6.9 | 8.9 | 10.9 | 25.0 |

F. Evaluation of ipfencarbazone biostimulant effect in wheat, *sorghum*, corn, soybean, dry bean and cotton—Early POST emergency application is shown below.

TABLE 12

Crop Code

TRZAX, BCER, *Triticum aestivum*, = US
SORVU, BGRM, *Sorghum bicolor*, = US
ZEAMX, BCOR, *Zea mays*, = US
PHSVX, BVBE, *Phaseolus vulgaris*, = US
GLXMA, BSOY, *Glycine max*, = US
GOSHI, BCOT, *Gossypium hirsutum*, = US
BRADC, BGRM, *Brachiaria decumbens*, = US
Part Rated PLANT = plant
C = Crop is Part Rated
Rating Type HEIGHT = height
Rating Unit cm = centimeter
PLANT = plant/plant biomass/shrub
ARM Action Codes APoC = Automatic percent control (Control forced to 100% on AOV Means Table)
AS = Automatic square root transformation of X + 0.5

What is claimed is:

1. A method of stimulating or promoting crop plant growth comprising applying to the crop plant a composition comprising about 5 to about 60 wt. % ipfencarbazone and a surfactant,
   wherein the crop plant is corn, wheat, sorghum or grass, and the ipfencarbazone is applied to the crop plant in an amount of about 60 grams per hectare to about 125 grams per hectare to stimulate or promote plant growth, or
   wherein the crop plant is soybeans, dry beans or cotton, and the ipfencarbazone is applied to the crop plant in an amount of about 60 grams per hectare to about 250 grams per hectare to stimulate or promote plant growth; and
   wherein stimulating or promoting plant growth is assessed by an increase of about 105% to about 400% of at least one of plant height, leaf area, biomass, plant vigor, and plant color as compared to an untreated control wherein the ipfencarbazone is effective in the stimulating or promoting the plant growth.

2. The method of claim 1, wherein the applying step is carried out post-emergence.

3. The method of claim 1, wherein the applying step comprises a pre-emergence application.

4. The method of claim 1, wherein the composition further comprises a second active.

5. The method of claim 4, wherein the second active is selected from the group consisting of amicarbazone, carfentrazone, clethodim, flucarbazone, flumioxazin, isoxaflutole, mesotrione, and quizalofop.

6. The method of claim 1, wherein the surfactant is a non-ionic surfactant.

7. The method of claim 6, wherein the non-ionic surfactant is selected from the group consisting of ethoxylated fatty acids, alcohol ethoxylates, tristyrylphenol ethoxylates, ethoxylated sorbitan fatty acid esters, and mixtures thereof.

8. The method of claim 1, wherein the composition comprises a further plant growth stimulant or promoter.

9. The method of claim 8, wherein the growth stimulant or promoter is selected from the group consisting of ancymidol, butralin, alcohols, chlormequat chloride, cytokinin, daminozide, ethephon, ethylene, flurprimidol, gibberellic acid, gibberellin mixtures, indole-3-butyric acid (IBA), maleic hydrazide, potassium salt, mefluidide, mepiquat chloride, mepiquat pentaborate, naphthalene-acetic acid (NAA), 1-naphthaleneacetamide (NAD), n-decanol, paclobutrazol, prohexadione calcium, trinexapac-ethyl, and uniconazole.

10. The method of claim 2, wherein post-emergence comprises seedling stage of the crop plant.

11. The method of claim 1, wherein the composition is provided as a concentrate and a diluting step is performed prior to the applying step thereby providing a diluted composition.

12. The method of claim 11, wherein the applying step comprises spraying the diluted composition.

13. The method of claim 1, wherein the composition comprises a diluent.

14. The method of claim 13, wherein the diluent is selected from the group consisting of water, an aliphatic hydrocarbon, an aromatic hydrocarbon, and an alkyl ester.

15. The method of claim 1, wherein enhanced plant height is an increase in height from about 105 percent to about 400 percent of the control.

16. The method of claim 1, wherein enhanced plant height is an increase in height from about 120 percent to about 350 percent of the control.

17. The method of claim 1, wherein ipfencarbazone improves nitrogen uptake by plants.

18. The method of claim 1, wherein the method comprises treating a seed of a plant.

19. The method of claim 5, wherein the composition comprises a further plant growth stimulant or promoter.

20. A method for stimulating or promoting plant growth in a crop plant, the method comprising applying, post emergence, a composition comprising about 60 grams per hectare to about 125 grams per hectare of a composition comprising ipfencarbazone; a second active selected from the group consisting of amicarbazone, carfentrazone, clethodim, flucarbazone, flumioxazin, isoxaflutole, mesotrione, quizalofop; and a non-ionic surfactant; wherein the crop plant is corn, wheat, sorghum or grass wherein the ipfencarbazone is effective in the stimulating or promoting the plant growth.

21. The method of claim 20, wherein the non-ionic surfactant is selected from the group consisting of ethoxylated fatty acids, alcohol ethoxylates, tristyrylphenol ethoxylates, ethoxylated sorbitan fatty acid esters, and mixtures thereof.

22. The method of claim 20, wherein the concentration of ipfencarbazone is in a range from about 1 percent by weight of the composition to about 80 percent by weight of the composition.

23. The method of claim 20, wherein stimulating or promoting plant growth is assessed by enhanced plant height, leaf area, biomass, plant vigor, plant color, or combinations thereof.

24. The method of claim 20, wherein ipfencarbazone improves nitrogen uptake by plants.

25. The method of claim 20, wherein the method comprises treating a seed of a plant.

26. The method of claim 20, wherein the composition comprises a further plant growth stimulant or promoter.

27. A method of stimulating or promoting crop plant growth comprising applying to a crop plant a composition comprising about 5 to about 60 wt. % ipfencarbazone,
wherein the composition does not contain a surfactant; and
wherein the crop plant is corn, wheat, sorghum or grass, and the ipfencarbazone is applied to the crop plant in an amount of about 60 grams per hectare to about 125 grams per hectare to stimulate or promote plant growth, or
wherein the crop plant is soybeans, dry beans or cotton, and the ipfencarbazone is applied to the crop plant in an amount of about 60 grams per hectare to about 250 grams per hectare to stimulate or promote plant growth; and
wherein stimulating or promoting plant growth is assessed by an increase of about 105% to about 400% of at least one of plant height, leaf area, biomass, plant vigor, and plant color as compared to an untreated control wherein the ipfencarbazone is effective in the stimulating or promoting the plant growth.

28. The method of claim 27, wherein the composition further comprises a second active.

29. The method of claim 28, wherein the second active is selected from the group consisting of amicarbazone, carfentrazone, clethodim, flucarbazone, flumioxazin, isoxaflutole, mesotrione, quizalofop, and combinations of the foregoing.

30. The method of claim 27, wherein the composition comprises a further plant growth stimulant or promoter.

31. The method of claim 30, wherein the growth stimulant or promoter is selected from the group consisting of ancymidol, butralin, alcohols, chlormequat chloride, cytokinin, daminozide, ethephon, ethylene, flurprimidol, gibberellic acid, gibberellin mixtures, indole-3-butyric acid (IBA), maleic hydrazide, potassium salt, mefluidide, mepiquat chloride, mepiquat pentaborate, naphthalene-acetic acid (NAA), 1-naphthaleneacetamide (NAD), n-decanol, paclobutrazol, prohexadione calcium, trinexapac-ethyl, and uniconazole.

32. A method of stimulating or promoting plant growth comprising applying to a crop plant a composition comprising about 5 to about 60 wt. % ipfencarbazone,
wherein the composition does not contain a surfactant; and
wherein ipfencarbazone is applied to the crop plant in an amount to stimulate or promote plant growth;
wherein the amount sufficient to stimulate or promote plant growth is in a range from 50 grams per hectare to 250 grams per hectare;
wherein the crop plant is soybeans, dry beans or cotton; and
wherein stimulating or promoting crop-plant growth is assessed by an increase of about 120% of at least one of plant height, leaf area, biomass, plant vigor, and plant color as compared to an untreated control wherein the ipfencarbazone is effective in the stimulating or promoting the plant growth.

* * * * *